(12) United States Patent
Achen et al.

(10) Patent No.: US 6,689,580 B1
(45) Date of Patent: Feb. 10, 2004

(54) GROWTH FACTOR

(75) Inventors: Marc G. Achen, North Melbourne (AU); Andrew F. Wilks, South Yarra (AU); Steven A. Stacker, North Fitzroy (AU); Kari Alitalo, Espoo (FI)

(73) Assignees: Ludwig Institute for Cancer Research, New York, NY (US); Helsinki University Licensing Ltd., Helsinki (FI)

( * ) Notice: Subject to any disclaimer, the term of this patent is extended or adjusted under 35 U.S.C. 154(b) by 0 days.

(21) Appl. No.: 09/296,275

(22) Filed: Apr. 22, 1999

Related U.S. Application Data

(62) Division of application No. 08/915,795, filed on Aug. 21, 1997, now Pat. No. 6,235,713.
(60) Provisional application No. 60/051,426, filed on Jul. 1, 1997, provisional application No. 60/038,814, filed on Feb. 10, 1997, provisional application No. 60/031,097, filed on Nov. 14, 1996, and provisional application No. 60/023,751, filed on Aug. 23, 1996.

(30) Foreign Application Priority Data

| Aug. 23, 1996 | (AU) | PO1825 |
| Nov. 11, 1996 | (AU) | PO3554 |
| Feb. 5, 1997 | (AU) | PO4954 |
| Jun. 19, 1997 | (AU) | PO7435 |

(51) Int. Cl.$^7$ ............ C12N 1/21; C12N 5/16; C12N 15/18; C12N 15/63; C12N 15/64
(52) U.S. Cl. ............ 435/69.1; 435/69.7; 435/325; 435/243; 435/320.1; 435/69.4; 536/23.1; 536/23.4; 536/23.51
(58) Field of Search ............ 435/69.1, 320.1, 435/325, 243; 536/23.1

(56) References Cited

U.S. PATENT DOCUMENTS 5,194,596 A * 3/1993 Tischer et al.

FOREIGN PATENT DOCUMENTS

| WO | 95/24473 | 9/1995 |
| WO | 96/26736 | 9/1996 |
| WO | 96/27007 | 9/1996 |
| WO | 96/39421 | 12/1996 |
| WO | 97/12972 | 4/1997 |
| WO | 98/02543 | 1/1998 |
| WO | 98/07832 | 2/1998 |
| WO | 98/24811 | 6/1998 |

OTHER PUBLICATIONS

Tischer, et al., Biochem. And Biophys. Research Communication, 163 (3) : 1198–1206, 1989.

Orlandini, et al., Proc. Natl. Acad. Of Science, USA 93:11675–11680, 1996.

Hillier, et al., GenBank Accession No. H24828, 1995.

* cited by examiner

*Primary Examiner*—Christine J. Saoud
(74) *Attorney, Agent, or Firm*—Crowell & Moring LLP

(57) ABSTRACT

VEGF-D, a new member of the PDGF family of growth factors, which among other things stimulates endothelial cell proliferation and angiogenesis and increases vascular permeability, as well as nucleotide sequences encoding it, methods for producing it, antibodies and other antagonists to it, transfected or transformed host cells for expressing it, pharmaceutical compositions containing it, and uses thereof in medical and diagnostic applications.

14 Claims, 19 Drawing Sheets

```
  1  M R S S Q S - - - - T L F R S E Q Q I R A A S S L E E L L R   VEGF-D
  1  M N F L L S W V H W S L A - - - - - - - - - - - L L L          h VEGF 165

27  I T H S E D W K L W R C R L R L K S F T S M D S R S A S H R   VEGF-D
 17  Y L H H A K W S - - - - - - - Q A A P M A E G G G Q N H H     h VEGF 165

57  S T - R F A A T F Y D I E T L K V I D E E W Q R T Q C S P R   VEGF-D
 39  E V V K F M D V Y - - - - - - - - - - - Q R S Y C H P I       h VEGF 165

86  E T C V E V A S E L G K S T N T F F K P P C V N V F R C G G   VEGF-D
 56  E T L V D I F Q E Y P D E I E Y I F K P S C V P L M R C G G   h VEGF 165

116  C C N E E S L I C M N T S T S Y I S K Q L F E I S V P L T S   VEGF-D
 86  C C N D E G L E C V P T E E S N I T M Q I M R I K P - - H Q   h VEGF 165

146  V P E L V P V K V A N H T G C K C L P T A P R H P Y S I I R   VEGF-D
114  G Q H I G E M S F L Q H N K C E C R P K K D R - - - - - - -   h VEGF 165

176  R S I Q I P E E D R C S H S K K L C P I D M L W D S N K C K   VEGF-D
137  - - - - - A R Q E N P C G P C - - - - - - - - - - - - - -     h VEGF 165

206  C V L Q E E N P L A G T E D H S H L Q E P A L C G P H M M F   VEGF-D
147  - - - - - - - - - - - S E R R K H L - - - - - - - - - - -     h VEGF 165

236  D E D R C E C V C K T P C P K D L I Q H P K N C S C F E C K   VEGF-D
154  - - - - - - - - - F V Q D P Q T C K C - S C K                 h VEGF 165

266  E S L E T C C Q K H K L F H P D T C S C E D R C P F H T R P   VEGF-D
167  N T D S R C K A R Q L E L N E R T C R C D - - - - - - - -     h VEGF 165

296  C A S G K T A C A K H C R F P K E K R A A Q G P H S R K N P   VEGF-D
188  - - - - - - - - - - - - - - - - - - - - - K P R R             h VEGF 165
```

FIG. 1A

```
1   MRSSQSTLERSEQQIRAASSLEELLRITHS         VEGF-D
1   MSPLLRRL----------LLAALLQLAPA           h VEGF-B

31  EDWKLWRCRLRLKSFTSMDSRSASHRSTRF          VEGF-D
20  QA----------PVSQPDAPGHQRKVVSW           h VEGF-B

61  AATFYDIETLKVIDEEWQRTQCSPRETCVE          VEGF-D
39  IDVY------------TRATCQPREVVVP           h VEGF-B

91  VASELGKSTNTFFKPPCVNVFRCGGCCNEE          VEGF-D
56  LTVELMGTVAKQLVPSCVTVQRCGGCCPDD          h VEGF-B

121 SLICMNTSTSYISKQLFEISVPLTSVPELV          VEGF-D
86  GLECVPTGQHQVRMQILMLRYPSSQLGEM-          h VEGF-B

151 PVKVANHTGCKCLPTAPRHPYSIIRRSIQI          VEGF-D
115 --SLEEHSQCECRPK----------KKDSAV         h VEGF-B

181 PEEDRCSHSKKLCPIDMLWDSNKCKCVLQE          VEGF-D
134 KPDS----PRPLCP------------RCTQHH        h VEGF-B

211 ENPLAGTEDHSHLQEPALCGPHMMFDEDRC          VEGF-D
150 QRP-----------------DPRTC               h VEGF-B

241 ECVCKTPCPKDLIQHPKNCSCFECKESLET          VEGF-D
158 RCRCRR---RSFLR----------                h VEGF-B

271 CCQKHKL-FHPDTCSCEDRCPFHTRPCASG          VEGF-D
169 -CQGRGLELNPDTCRC----------              h VEGF-B

300 KTACAKHCRFPKEKRAAQGPHSRKNP              VEGF-D
184 ----------------------RKLRR             h VEGF-B
```

FIG. 1B

```
  1  M R S S Q S T L E R S E Q Q I R A A S S L E E L L R I T H S   VEGF-D
  1  M T - - - - - - - - - - - - - - - - - - - - - - - - V L Y P   VEGF-C

31  E D W K L W R C R L R - - - - - - L K S F T S H D S R S A S   VEGF-D
  7  E Y H K M Y K C Q L R K G G W Q H N R E Q A N L N S R T E E   VEGF-C

55  H R S T R F A A T F Y D I E T L K V I D E E W Q R T Q C S P   VEGF-D
 37  - - T I K F A A A H Y N T E I L K S I D N E W R K T Q C M P   VEGF-C

85  R E T C V E V A S E L G K S T N T F F K P P C V N V F R C G   VEGF-D
 65  R E V C I D V G K E F G V A T N T F F K P P C V S V Y R C G   VEGF-C

115  G C C N E E S L I C M N T S T S Y I S K Q L F E I S V P L T   VEGF-D
 95  G C C N S E G L Q C M N T S T S Y L S K T L F E I T V P L S   VEGF-C

145  S V P E L V P V K V A N H T G C K C L P T A P - - R H P Y S   VEGF-D
125  Q G L P K P V T I S F A N H T S C R C M S K L D V Y R Q V H S   VEGF-C

173  I I R R S I Q I P E E D R C S H S K K L C P I D M L W D S N   VEGF-D
155  I I R R S L P A T L P Q - C Q A A N K T C P T N Y M W N N H   VEGF-C

203  K C K C V L Q E E - - - N P L A G T E D - - - - - - - - - -   VEGF-D
184  I C R C L A Q E D F M F S S D A G D D S T D G F H D I C G P   VEGF-C

220  H S H L Q E - - - - - - - - - - - - - - - - - - - - - - - -   VEGF-D
214  N K E L D E E T C Q C V C R A G L R P A S C G P H K E L D R   VEGF-C

226  - - - - - - - - - - - P A L C G P H M M F D E D R C E C V   VEGF-D
244  N S C Q C V C K N K L F P S Q C G A N R E F D E N T C Q C V   VEGF-C

244  C K T P C P K D L I Q H P K N C S C F E C K E S L E T C C Q   VEGF-D
274  C K R T C P R N Q P L N P G K C A C - E C T E S P Q K C L L   VEGF-C

274  K H K L F H P D T C S C E D R C P P H T R P C A S G K T A C   VEGF-D
303  K G K K F H H Q T C S C - - - - - - Y R R P C T N R Q K A C   VEGF-C

304  A K H C R F P K E K - R A A Q G P H S R K N P .                VEGF-D
327  E P G F S Y S E E V C R C V P S Y W K R R Q M S                VEGF-C
```

FIG. 1C

```
  1 MRSSQ---------STLERSEQQIRAASSL        VEGF-D
  1 MPVMRLFPCFLQLLAGLA------------        hPlGF

22 EELLRITHSEDWKLWRCRLRLKSFTSMDSR        VEGF-D
 19 ---LPAVPPQQWAL----------------        hPlGF

52 SASHRSTRFAATFYDIETLKVIDEEWQRTQ        VEGF-D
 30 SAGNGSS-------EVEVVP-FQEVWGRSY        hPlGF

82 CSPRETCVEVASELGKSTNTFFKPPCVNVF        VEGF-D
 52 CRALERLVDVVSEYPSEVEHMFSPSCVSLL        hPlGF

112 RCGGCCNEESLICMNTSTSYISKQLPEISV        VEGF-D
 82 RCTGCCGDENLHCVPVETANVTMQLLKIRS        hPlGF

142 PLTSVPELVPVKVANHTGCKCLPTAPRHPY        VEGF-D
112 --GDRPSYVELTFSQHVRCECRP-------        hPlGF

172 SIIRRSIQIPEEDRCSHSKKLCPIDMLWDS        VEGF-D
133 --LREKMK-PERRR----------------        hPlGF

202 NKCKCVLQEENPLAGTEDHSHLQEPALCGP        VEGF-D
144 -----------------------------        hPlGF

232 HMMFDEDRCECVCKTPCPKDLIQHPKNCSC        VEGF-D
144 -----------------------------        hPlGF

262 FECKESLETCCQKHKLFHPDTCSCEDRCPF        VEGF-D
144 -----------------------------        hPlGF

292 HTRPCASGKTACAKHCRFPKEKRAAQGP--        VEGF-D
144 -----PKGRG---------KRRREKQRPTD        hPlGF

320 -----HSRKNP                          VEGF-D
160 CHLCGDAVPRR                          hPlGF
```

```
  1  MRSSQSTLERSEQQIRAASSLEELLRITHS            VEGF-D
  1  MT- - - - - - - - - - - - - - - - - - - VLYP  VEGF-C
  1  MS- - - - - - - - - - - - - - - PT- - - -  h VEGF-B
  1  M- - - - - - - - - - - - - - NFLLS        h VEGF 165
  1  MP- - - - - - - - - - - - - VHRLPPC        hPlGF

31  EDWKLHRCRLRLKSF- - - - - -TSHDSRSA        VEGF-D
  7  EYHKHYTRCQLRKGGWQR- NREQANLNSRT-           VEGF-C
  5  - - - - LRRLLAALLQLAPAQAPVSQPDA            h VEGF-B
  7  - - WVHWSLALLLYLHHAKWSQAAPMAEGG            h VEGF 165
 10  - - PLQLLAGLALPAVPPQQWALSAGN                hPlGF

54  SHRSTRFAATFYDIETLKVIDEEWQRTQCS             VEGF-D
 35  - EETIKFAAAHYNTEILKSIDNEWRKTQCM             VEGF-C
 29  PGE- - - - - - - - QRKVVSWIDVYTRATCQ        h VEGF-B
 34  GQN- - - - - - - - HHEVVKFMDVYQRSYCH        h VEGF 165
 34  GSS- - - - - - - - EVEVVPFQEV-HCRSYCR       hPlGF

84  PRETCVEVASELGKSTNTFFKPPCVNVFRC             VEGF-D
 64  PREVCIDVGKEFGVALNTFFKPPCVSVYRC             VEGF-C
 49  PREVVPLTVELMGTVAKQLVPSCVTVQRC              h VEGF-B
 54  PIETLVDIFQEYPDEIEYIFKPSCVPLMRC             h VEGF 165
 54  ALERLVDVVSEYPSEVEHMFSPSCVSLLRC             hPlGF

114  GGCNDESLICHNTSTSYISKQLFEISVPL              VEGF-D
 94  GGCNSDGLQCMNTSTSYLSKTLFEITVPL              VEGF-C
 79  GGCPDDGLECVPTGQHQVRMQILMIR- - -             h VEGF-B
 84  GGCNDEGLECVPTEESNITMQIMRIKP- -             h VEGF 165
 84  TGCCGDENLHCVPVETANVTMQLLKIRS- -             hPlGF

144  TSYPELVPVKVANHTGCKCLPTAP- -RHPY             VEGF-D
124  SQGPKPVTISFANHTSCRCHSKLDVYRQVH              VEGF-C
106  YPSSQLGEMSLEESQCEC- - - - - - - -           h VEGF-B
112  HQGQHIGEMSFLQHNKCEC- - - - - - v            h VEGF 165
112  GDRPSYVELTFSQHVRCEC- - - - - - - -          hPlGF

172  SIIRRSIQTPEEDRCSHSKKLCPIDMLWDS             VEGF-D
154  SIIRRSLP- ATLPQCQAANKTCPTNYMWNN             VEGF-C
125  - - - RPKKKDSAVKPDSPRPLCP- - - - -          h VEGF-B
131  - - - RPKKDR- - ARQENP- - -CG- - - - -      h VEGF 165
131  - - - RPLREK- -MK- - - - - - - - - -         hPlGF

202  NKCKCVLQEENPLAGTED- - - - - - -             VEGF-D
183  HICRCLAQEDFKFSSDAGDDSTDGFHDICG             VEGF-C
144  - - -RCTQEHQR- - -P- - - - - - - -          h VEGF-B
145  - - -PCSERRKHLFVQ- - - - - - - - -          h VEGF 165
139  - - - - -PERRRP- - - - - - - - - -          hPlGF

220  - HSHLQE- - - - - - - - - - - -             VEGF-D
213  PNKELDEETCQCVCRAGLRPASCGPHKELD             VEGF-C
153  - - - - - - - - - - - - - - - - - -D        h VEGF-B
157  - - - - - - - - - - - - - - - - - -D        h VEGF 165
145  - - - - - - - - - - - - - - - - - -          hPlGF

226  - - - - - - - -PALCGPHMMFDEDRCLC             VEGF-D
243  RNSCQCVCKNKLFPSQCGANREENTCQC              VEGF-C
154  PRTCRCECRRRSF- - - - - - - - -             h VEGF-B
158  PQTCKCSCKNTD- - - - - - - - - -             h VEGF 165
145  - - - - - - -KGRG- - - - - - - - -           hPlGF

243  VCKTPCPKDLIQHPKNCSCFECKESLETCC             VEGF-D
273  VCKRTCPRNQPLNPGKCACECTESPQKCL              VEGF-C
167  - - - - - - - - - - - - - - - -LRCQ         h VEGF-B
170  - - - - - - - - - - - - - - - -SRCK         h VEGF 165
149  - - - - - - - - - - - - - - - -KRRR         hPlGF

273  QKHKLFHPDTCSCEDR- CPHTRPCASGKT             VEGF-D
302  LKGKRFHHQTCSCYRRPCTNRQKACEPGFS             VEGF-C
171  GRGLELNPDTCRC- - - - - - - - -             h VEGF-B
174  ARQLELNERTCRC- - - - - - - - -             h VEGF 165
153  EKQRPTDCHLCGD- - - - - - - - -               hPlGF

302  ACAKHCRFPKFPPAAQGPHSRKNP                    VEGF-D
332  YSEEVCRCVPSYW- - - - -KRPQHS                VEGF-C
184  - - - - - - - - - - - - -RKLRR              h VEGF-B
187  - - - - - - - - - - - - -DKPRR              h VEGF 165
166  - - - - - - - - - - - - -AVPRR               hPlGF
```

FIG. 3

```
         10         20         30         40
MRSSQSTLERSEQQIRAASSLEELLRITHSEDWKLWRCRL 50         60         70         80
RLKSFTSMDSRSASHRSTRFAATFYDIETLKVIDEEWQRT 90        100        110        120
QCSPRETCVEVASELGKSTNTFFKPPCVNVFRCGGCCNEE 130        140        150        160
SLICMNTSTSYISKQLFEISVPLTSVPELVPVKVANHTGC 170        180        190        200
KCLPTAPRHPYSIIRRSIQIPEEDRCSHSKKLCPIDMLWD 210        220        230        240
SNKCKCVLQEENPLAGTEDHSHLQEPALCGPHMMFDEDRC 250        260        270        280
ECVCKTPCPKDLIQHPKNCSCFECKESLETCCQKHKLFHP 290        300        310        320
DTCSCEDRCPFHTRPCASGKTACAKHCRFPKEKRAAQGPH

SRKNP
```

FIG. 4

```
GTTGGGTTCCAGCTTTCTGTAGCTGTAAGCATTGGTGGCCACACCACCTCCTTACAA
AGCAACTAGAACCTGCGGCATACATTGGAGAGATTTTTTTAATTTTCTGGACATGAA
GTAAATTTAGAGTGCTTTCTAATTTCAGGTAGAAGACATGTCCACCTTCTGATTATT
TTTGGAGAACATTTTGATTTTTTTCATCTCTCTCTCCCCACCCCTAAGATTGTGCAA
AAAAAGCGTACCTTGCCTAATTGAAATAATTTCATTGGATTTTGATCAGAACTGATT
ATTTGGTTTTCTGTGTGAAGTTTTGAGGTTTCAAACTTTCCTTCTGGAGAATGCCTT
TTGAAACAATTTTCTCTAGCTGCCTGATGTCAACTGCTTAGTAATCAGTGGATATTG
AAATATTCAAAATGTACAGAGAGTGGGTAGTGGTGAATGTTTTCATGATGTTGTACG
TCCAGCTGGTGCAGGGCTCCAGTAATGAACATGGACCAGTGAAGCGATCATCTCAGT
CCACATTGGAACGATCTGAACAGCAGATCAGGGCTGCTTCTAGTTTGGAGGAACTAC
TTCGAATTACTCACTCTGAGGACTGGAAGCTGTGGAGATGCAGGCTGAGGCTCAAAA
GTTTTACCAGTATGGACTCTCGCTCAGCATCCCATCGGTCCACTAGGTTTGCGGCAA
CTTTCTATGACATTGAAACACTAAAAGTTATAGATGAAGAATGGCAAAGAACTCAGT
GCAGCCCTAGAGAAACGTGCGTGGAGGTGGCCAGTGAGCTGGGGAAGAGTACCAACA
CATTCTTCAAGCCCCCTTGTGTGAACGTGTTCCGATGTGGTGGCTGTTGCAATGAAG
AGAGCCTTATCTGTATGAACACCAGCACCTCGTACATTTCCAAACAGCTCTTTGAGA
TATCAGTGCCTTTGACATCAGTACCTGAATTAGTGCCTGTTAAAGTTGCCAATCATA
CAGGTTGTAAGTGCTTGCCAACAGCCCCCGCCATCCATACTCAATTATCAGAAGAT
CCATCCAGATCCCTGAAGAAGATCGCTGTTCCCATTCCAAGAAACTCTGTCCTATTG
ACATGCTATGGGATAGCAACAAATGTAAATGTGTTTTGCAGGAGGAAAATCCACTTG
CTGGAACAGAAGACCACTCTCATCTCCAGGAACCAGCTCTCTGTGGGCCACACATGA
TGTTTGACGAAGATCGTTGCGAGTGTGTCTGTAAAACACCATGTCCCAAAGATCTAA
TCCAGCACCCCAAAAACTGCAGTTGCTTTGAGTGCAAAGAAAGTCTGGAGACCTGCT
GCCAGAAGCACAAGCTATTTCACCCAGACACCTGCAGCTGTGAGGACAGATGCCCCT
TTCATACCAGACCATGTGCAAGTGGCAAAACAGCATGTGCAAAGCATTGCCGCTTTC
CAAAGGAGAAAAGGGCTGCCCAGGGGCCCCACAGCCGAAAGAATCCTTGATTCAGCG
TTCCAAGTTCCCCATCCCTGTCATTTTTAACAGCATGCTGCTTTGCCAAGTTGCTGT
CACTGTTTTTTTCCCAGGTGTTAAAAAAAAAATCCATTTTACACAGCACCACAGTGA
ATCCAGACCAACCTTCCATTCACACCAGCTAAGGAGTCCCTGGTTCATTGATGGATG
TCTTCTAGCTGCAGATGCCTCTGCGCACCAAGGAATGGAGAGGAGGGGACCCATGTA
ATCCTTTTGTTTAGTTTTGTTTTTGTTTTTGGTGAATGAGAAAGGTGTGCTGGTCA
TGGAATGGCAGGTGTCATATGACTGATTACTCAGAGCAGATGAGGAAAACTGTAGTC
TCTGAGTCCTTTGCTAATCGCAACTCTTGTGAATTATTCTGATTCTTTTTTATGCAG
AATTTGATTCGTATGATCAGTACTGACTTTCTGATTACTGTCCAGCTTATAGTCTTC
CAGTTTAATGAACTACCATCTGATGTTTCATATTTAAGTGTATTTAAAGAAAATAAA
CACCATTATTCAAGCCAAAAAAAAAAAAAAAAAAA
```

MYREWVVVNVFMMLYVQLVQGSSNEHGPVKRSSQSTLERSEQQIRAASSLEELLRIT
HSEDWKLWRCRLRLKSFTSMDSRSASHRSTRFAATFYDIETLKVIDEEWQRTQCSPR
ETCVEVASELGKSTNTFFKPPCVNVFRCGGCCNEESLICMNTSTSYISKQLFEISVP
LTSVPELVPVKVANHTGCKCLPTAPRHPYSIIRRSIQIPEEDRCSHSKKLCPIDMLW
DSNKCKCVLQEENPLAGTEDHSHLQEPALCGPHMMFDEDRCECVCKTPCPKDLIQHP
KNCSCFECKESLETCCQKHKLFHPDTCSCEDRCPFHTRPCASGKTACAKHCRFPKEK
RAAQGPHSRKNP

```
GGAGAATGCCTTTTGCAACACTTTTCAGTAGCTGCCTGGAAACAACTGCTTAGTCAT
CGGTAGACATTTAAAATATTCAAAATGTATGGAGAATGGGGAATGGGGAATATCCTC
ATGATGTTCCATGTGTACTTGGTGCAGGGCTTCAGGAGCGAACATGGACCAGTGAAG
GATTTTTCTTTTGAGCGATCATCCCGGTCCATGTTGGAACGATCTGAACAACAGATC
CGAGCAGCTTCTAGTTTGGAGGAGTTGCTGCAAATCGCGCACTCTGAGGACTGGAAG
CTGTGGCGATGCCGGTTGAAGCTCAAAAGTCTTGCCAGTATGGACTCACGCTCAGCA
TCCCATCGCTCCACCAGATTTGCGGCAACTTTCTATGACACTGAAACACTAAAAGTT
ATAGATGAAGAATGGCAGAGGACCCAATGCAGCCCTAGAGAGACATGCGTAGAAGTC
GCCAGTGAGCTGGGGAAGACAACCAACACATTCTTCAAGCCCCCCTGTGTAAATGTC
TTCCGGTGTGGAGGCTGCTGCAACGAAGAGGGTGTGATGTGTATGAACACAAGCACC
TCCTACATCTCCAAACAGCTCTTTGAGATATCAGTGCCTCTGACATCAGTGCCCGAG
TTAGTGCCTGTTAAAATTGCCAACCATACGGGTTGTAAGTGCTTGCCCACGGGCCCC
CGCCATCCTTACTCAATTATCAGAAGATCCATTCAGACCCCAGAAGAAGATGAATGT
CCTCATTCCAAGAAACTCTGTCCTATTGACATGCTGTGGGATAACACCAAATGTAAA
TGTGTTTTGCAAGACGAGACTCCACTGCCTGGGACAGAAGACCACTCTTACCTCCAG
GAACCCACTCTCTGTGGACCGCACATGACGTTTGATGAAGATCGCTGTGAGTGCGTC
TGTAAAGCACCATGTCCGGGAGATCTCATTCAGCACCCGGAAAACTGCAGTTGCTTT
GAGTGCAAAGAAAGTCTGGAGAGCTGCTGCCAAAAGCACAAGATTTTTCACCCAGAC
ACCTGCAGCTGTGAGGACAGATGTCCTTTTCACACCAGAACATGTGCAAGTAGAAAG
CCAGCCTGTGGAAAGCACTGGCGCTTTCCAAAGGAGACAAGGGCCCAGGGACTCTAC
AGCCAGGAGAACCCTTGATTCAACTTCCTTTCAAGTCCCCCCATCTCTGTCATTTTA
AACAGCTCACTGCTTTGTCAAGTTGCTGTCACTGTTGCCCACTACCCCTTGAACATG
TGCAAACACAGACACACACACACACACACACAGAGCAACTAGAATTATGTTTTCT
AGGTGCTGCCTAAG
```

FIG. 7

```
AAACTTTGCTTCTGGAGAATGCCTTTTGCAACACTTTTCAGTAGCTGCCTGGAAACA
ACTGCTTAGTCATCGGTAGACATTTAAAATATTCAAAATGTATGGAGAATGGGGAAT
GGGGAATATCCTCATGATGTTCCATGTGTACTTGGTGCAGGGCTTCAGGAGCGAACA
TGGACCAGTGAAGCGATCATCCCGGTCCATGTTGGAACGATCTGAACAACAGATCCG
AGCAGCTTCTAGTTTGGAGGAGTTGCTGCAAATCGCGCACTCTGAGGACTGGAAGCT
GTGGCGATGCCGGTTGAAGCTCAAAAGTCTTGCCAGTATGGACTCACGCTCAGCATC
CGATCGCTCCACCAGATTTGCGGCAACTTTCTATGACACTGAAACACTAAAAGTTAT
AGATGAAGAATGGCAGAGGACCCAATGCAGCCCTAGAGAGACATGCGTAGAAGTCGC
CAGTGAGCTGGGGAAGACAACCAACACATTCTTCAAGCCCCCCTGTGTAAATGTCTT
CCGGTGTGGAGGCTGCTGCAACGAAGAGGGTGTGATGTGTATGAACACAAGCACCTC
CTACATCTCCAAACAGCTCTTTGAGATATCAGTGCCTCTGACATCAGTGCCCGAGTT
AGTGCCTGTTAAAATTGCCAACCATACGGGTTGTAAGTGCTTGCCCACGGGCCCCCG
CCATCCTTACTCAATTATCAGAAGATCCATTCAGACCCCAGAAGAAGATGAATGTCC
TCATTCCAAGAAACTCTGTCCTATTGACATGCTGTGGGATAACACCAAATGTAAATG
TGTTTTGCAAGACGAGACTCCACTGCCTGGGACAGAAGACCACTCTTACCTCCAGGA
ACCCACTCTCTGTGGACCGCACATGACGTTTGATGAAGATCGCTGTGAGTGCGTCTG
TAAAGCACCATGTCCGGGAGATCTCATTCAGCACCCGGAAAACTGCAGTTGCTTTGA
GTGCAAAGAAAGTCTGGAGAGCTGCTGCCAAAAGCACAAGATTTTTCACCCAGACAC
CTGCAGGTCAATGGTCTTTTCGCTTTCCCCTTAACTTGGTTTACTGATGACATTTAA
AGGACATACTAATCTGATCTGTTCAGGCTCTTTTCTCTCAGAGTCCAAGCAC
```

```
  1  M Y G E W G M G N I L M M F H V Y L V Q Q F R S E H G P V K D F S F E R S S R S  mVEGF-D1
  1  M Y G E W G M G N I L M M F H V Y L V Q Q F R S E H G P V K . . . . R S S R S  mVEGF-D2

41  M L E R S E Q Q I R A A S L E E L L Q I A H S E D W K L W R C R L K L K S L A  mVEGF-D1
 36  M L E R S E Q Q I R A A S L E E L L Q I A H S E D W K L W R C R L K L K S L A  mVEGF-D2

81  S M D S R S A S H R S T R F A A T F Y D T E T L K V I D E E W Q R T Q C S P R E  mVEGF-D1
 76  S M D S R S A S H R S T R F A A T F Y D T E T L K V I D E E W Q R T Q C S P R E  mVEGF-D2

121  T C V E V A S E L G K T T N T F F K P P C V N V F R C G G C C N E E G V M C M N  mVEGF-D1
116  T C V E V A S E L G K T T N T F F K P P C V N V F R C G G C C N E E G V M C M N  mVEGF-D2

161  T S T S Y I S K Q L F E I S V P L T S V P E L V P V K I A N H T G C K C L P T G  mVEGF-D1
156  T S T S Y I S K Q L F E I S V P L T S V P E L V P V K I A N H T G C K C L P T G  mVEGF-D2

201  P R H P Y S I I R R S I Q T P E E D E C P R S K K L C P I D M L W D N T K C K C  mVEGF-D1
196  P R H P Y S I I R R S I Q T P E E D E C P R S K K L C P I D M L W D N T K C K C  mVEGF-D2

241  V L Q D E T P L P G T E D H S Y L Q E P T L C G P H M T F D E D R C E C V C K A  mVEGF-D1
236  V L Q D E T P L P G T E D H S Y L Q E P T L C G P H M T P D E D R C E C V C K A  mVEGF-D2

281  P C P G D L I Q H P E N C S C F E C K E S L E S C C Q K H K I F H P D T C S C E  mVEGF-D1
276  P C P G D L I Q H P E N C S C F E C K E S L E S C C Q K H K I F H P D T C R S M  mVEGF-D2

321  D R C P P H T C A S R K P A C G K H W R P P K E T R A Q G L Y S Q N P  mVEGF-D1
316  . . . . . . . . . . . . . . . . . . . . . . . . . . V F S L . S P    mVEGF-D2
```

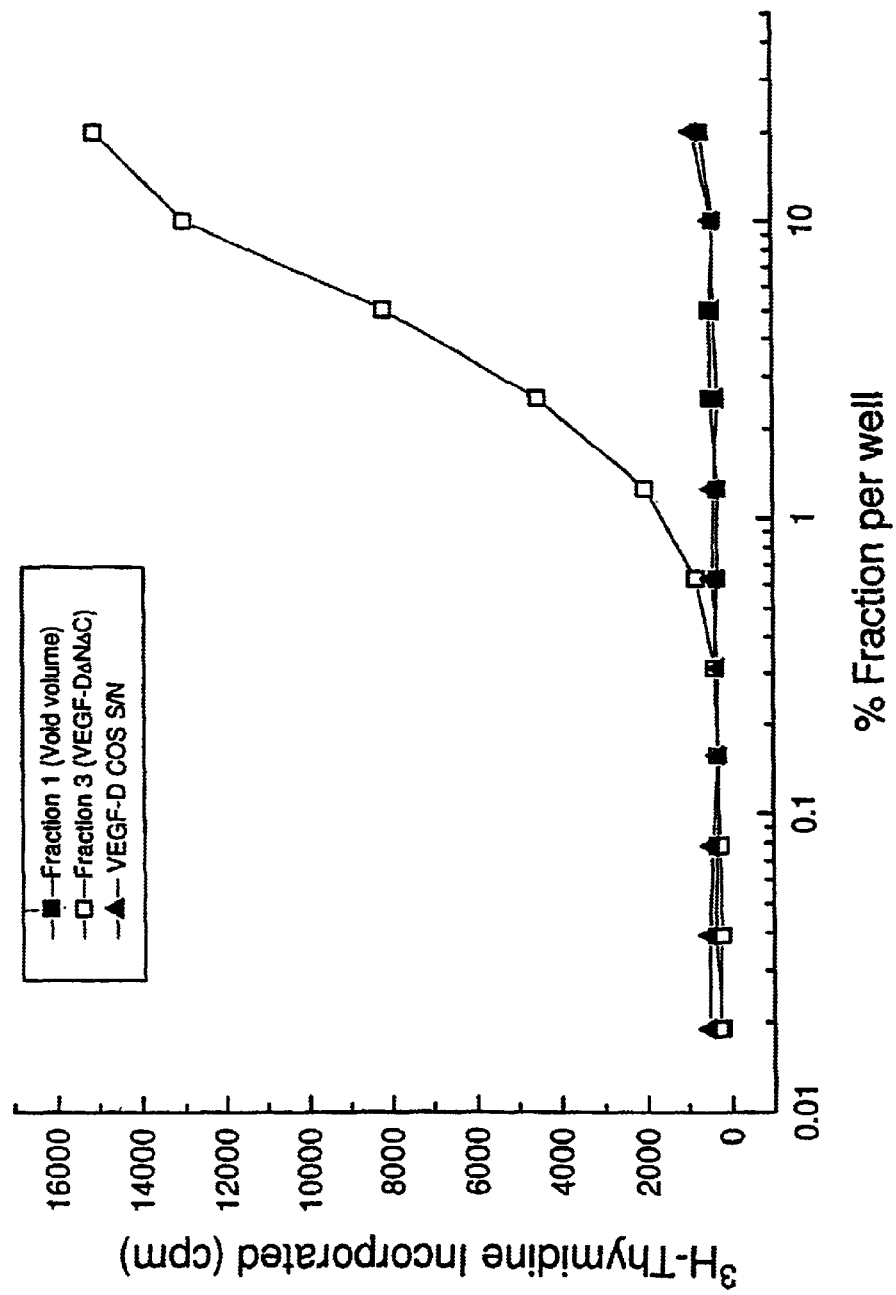

FIG. 15

GROWTH FACTOR

CROSS REFERENCE TO RELATED APPLICATIONS

This application is a division of application Ser. No. 08/915,795, filed Aug. 21, 1997, now U.S. Pat. No. 6,235,713. This application also claims the benefit of the filing dates of the following U.S. Provisional Application: Serial No. 60/023,751, filed Aug. 23, 1996; U.S. Provisional Application Serial No. 60/031,097, filed Nov. 14, 1996; U.S. Provisional Application Serial No. 60/038,814, filed Feb. 10, 1997; and U.S. Provisional Application Serial No. 60/051,426, filed Jul. 1, 1997.

FIELD OF THE INVENTION

This invention relates to growth factors for endothelial cells, and in particular to a novel vascular endothelial growth factor, DNA encoding the factor, and to pharmaceutical and diagnostic compositions and methods utilising or derived from the factor.

BACKGROUND OF THE INVENTION

Angiogenesis is a fundamental process required for normal growth and development of tissues, and involves the proliferation of new capillaries from pre-existing blood vessels. Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis which takes place in the normal individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes.

On the other hand, promotion of angiogenesis is desirable in situations where vascularization is to be established or extended, for example after tissue or organ transplantation, or to stimulate establishment of collateral circulation in tissue infarction or arterial stenosis, such as in coronary heart disease and thromboangitis obliterans.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor α (TGFα), and hepatocyte growth factor (HGF). See for example Folkman et al, "Angiogenesis", J. Biol. Chem., 1992 267 10931–10934 for a review.

It has been suggested that a particular family of endothelial cell-specific growth factors and their corresponding receptors is primarily responsible for stimulation of endothelial cell growth and differentiation, and for certain functions of the differentiated cells. These factors are members of the PDGF family, and appear to act via endothelial receptor tyrosine kinases (RTKs). Hitherto four vascular endothelial growth factor subtypes have been identified. Vascular endothelial growth factor (VEGF), now known as VEGF-A, has been isolated from several sources. VEGF-A shows highly specific mitogenic activity against endothelial cells, and can stimulate the whole sequence of events leading to angiogenesis. In addition, it has strong chemoattractant activity towards monocytes, can induce plasminogen activator and plasminogen activator inhibitor in endothelial cells, and can also influence microvascular permeability. Because of the latter activity, it is also sometimes referred to as vascular permeability factor (VPF). The isolation and properties of VEGF have been reviewed; see Ferrara et al, "The Vascular Endothelial Growth Factor Family of Polypeptides", J. Cellular Biochem., 1991 47 211–218 and Connolly, "Vascular Permeability Factor: A Unique Regulator of Blood Vessel Function", J. Cellular Biochem., 1991 47 219–223.

More recently, three further members of the VEGF family have been identified. These are designated VEGF-B, described in International Patent Application No. PCT/US96/02957 (WO 96/26736) by Ludwig Institute for Cancer Research and The University of Helsinki, VEGF-C, described in Joukov et al, The EMBO Journal, 1996 15 290–298, and VEGF2, described in International Patent Application No. PCT/US94/05291 (WO 95/24473) by Human Genome Sciences, Inc. VEGF-B has closely similar angiogenic and other properties to those of VEGF, but is distributed and expressed in tissues differently from VEGF. In particular, VEGF-B is very strongly expressed in heart, and only weakly in lung, whereas the reverse is the case for VEGF. This suggests that VEGF and VEGF-B, despite the fact that they are co-expressed in many tissues, may have functional differences.

VEGF-B was isolated using a yeast co-hybrid interaction trap screening technique, screening for cellular proteins which might interact with cellular retinoic acid-binding protein type I (CRABP-I). Its isolation and characteristics are described in detail in PCT/US96/02597 and in olofsson et al, Proc. Natl. Acad. Sci., 1996 93 2576–2581.

VEGF-C was isolated from conditioned media of PC-3 prostate adenocarcinoma cell line (CRL1435) by screening for ability of the medium to produce tyrosine phosphorylation of the endothelial cell-specific receptor tyrosine kinase Flt-4, using cells transfected to express Flt-4. VEGF-C was purified using affinity chromatography with recombinant Flt-4, and was cloned from a PC-3 cDNA library. Its isolation and characteristics are described in detail in Joukov et al, The EMBO Journal, 1996 15 290–298.

VEGF2 was isolated from a highly tumorgenic, oestrogen-independent human breast cancer cell line. While this molecule is stated to have about 22% homology to PDGF and 30% homology to VEGF, the method of isolation of the gene encoding VEGF2 is unclear, and no characterization of the biological activity is disclosed.

Vascular endothelial growth factors appear to act by binding to receptor tyrosine kinases of the PDGF-receptor family. Five endothelial cell-specific receptor tyrosine kinases have been identified, namely Flt-1 (VEGFR-1), KDR/Flk-1 (VEGFR-2), Flt-4 (VEGFR-3), Tie and Tek/Tie-2. All of these have the intrinsic tyrosine kinase activity which is necessary for signal transduction. The essential, specific role in vasculogenesis and angiogenesis of Flt-1, Flk-1, Tie and Tek/Tie-2 has been demonstrated by targeted mutations inactivating these receptors in mouse embryos. VEGFR-1 and VEGFR-2 bind VEGF with high affinity, and VEGFR-1 also binds VEGF-B and placenta growth factor (PlGF). VEGF-C has been shown to be the ligand for Flt-4 (VEGFR-3), and also activates VEGFR-2 (Joukov et al, 1996). A ligand for Tek/Tie-2 has been described (International Patent Application No. PCT/US95/12935

(WO 96/11269) by Regeneron Pharmaceuticals, Inc.); however, the ligand for Tie has not yet been identified.

The receptor Flt-4 is expressed in venous and lymphatic endothelia in the fetus, and predominantly in lymphatic endothelia in the adult (Kaipainen et al, Cancer Res, 1994 54 6571–6577; Proc Natl. Acad. Sci. USA, 1995 92 3566–3570). It has been suggested that VEGF-C may have a primary function in lymphatic endothelium, and a secondary function in angiogenesis and permeability regulation which is shared with VEGF (Joukov et al, 1996).

We have now isolated human cDNA encoding a novel protein of the vascular endothelial growth factor family. The novel protein, designated VEGF-D, has structural similarities to other members of this family.

SUMMARY OF THE INVENTION

The invention generally provides an isolated novel growth factor which has the ability to stimulate and/or enhance proliferation or differentiation of endothelial cells, isolated DNA sequences encoding the novel growth factor, and compositions useful for diagnostic and/or therapeutic applications.

According to one aspect, the invention provides an isolated and purified nucleic acid molecule which encodes a novel polypeptide, designated VEGF-D, which is structurally homologous to VEGF, VEGF-B and VEGF-C. In a preferred embodiment, the nucleic acid molecule is a cDNA which comprises the sequence set out in SEQ ID NO:1, SEQ ID NO:4, SEQ ID NO:6 or SEQ ID NO:7. This aspect of the invention also encompasses DNA molecules of sequence such that they hybridize under stringent conditions with DNA of SEQ ID NO:1, SEQ ID NO:4, SEQ ID NO:6 or SEQ ID NO:7. Preferably the DNA molecule able to hybridize under stringent conditions encodes the portion of VEGF-D from amino acid residue 93 to amino acid residue 201, optionally operatively linked to a DNA sequence encoding FLAG™ peptide.

Preferably the cDNA comprises the sequence set out in SEQ ID NO:4, SEQ ID NO:6 or SEQ ID NO:7, more preferably that of SEQ ID NO:4.

According to a second aspect, the invention provides a polypeptide possessing the characteristic amino acid sequence:

Pro-Xaa-Cys-Val-Xaa-Xaa-Xaa-Arg-Cys-Xaa-Gly-Cys-Cys (SEQ ID NO:2), said polypeptide having the ability to stimulate proliferation of endothelial cells, and said polypeptide comprising a sequence of amino acids substantially corresponding to the amino acid sequence set out in SEQ ID NO:3, or a fragment or analogue thereof which has the ability to stimulate one or more of endothelial cell proliferation, differentiation, migration or survival.

These abilities are referred to herein as "biological activities of VEGF-D" and can readily be tested by methods known in the art. Preferably the polypeptide has the ability to stimulate endothelial cell proliferation or differentiation, including, but not limited to, proliferation or differentiation of vascular endothelial cells and/or lymphatic endothelial cells.

More preferably the polypeptide has the sequence set out in SEQ ID NO:5, SEQ ID NO:8 or SEQ ID NO:9, and most preferably has the sequence set out in SEQ ID NO:5.

A preferred fragment of the polypeptide invention is the portion of VEGF-D from amino acid residue 93 to amino acid residue 201, optionally linked to FLAG™ peptide. Where the fragment is linked to FLAG™, the fragment is VEGFDΔNΔC, as hereindefined.

Thus polypeptides comprising conservative substitutions, insertions, or deletions, but which still retain the biological activity of VEGF-D, are clearly to be understood to be within the scope of the invention. The person skilled in the art will be well aware of methods which can readily be used to generate such polypeptides, for example the use of site-directed mutagenesis, or specific enzymic cleavage and ligation. The skilled person will also be aware that peptidomimetic compounds or compounds in which one or more amino acid residues are replaced by a non-naturally occurring amino acid or an amino acid analogue may retain the required aspects of the biological activity of VEGF-D. Such compounds can readily be made and tested by methods known in the art, and are also within the scope of the invention.

In addition, variant forms of the VEGF-D polypeptide which result from alternative splicing, as are known to occur with VEGF, and naturally-occurring allelic variants of the nucleic acid sequence encoding VEGF-D are encompassed within the scope of the invention. Allelic variants are well known in the art, and represent alternative forms or a nucleic acid sequence which comprise substitution, deletion or addition of one or more nucleotides, but which do not result in any substantial functional alteration of the encoded polypeptide.

As used herein, the term "VEGF-D" collectively refers to the polypeptides of SEQ ID NO:3, SEQ ID NO:5, SEQ ID NO:8 and SEQ ID NO:9 and fragments or analogues thereof which have the biological activity of VEGF-D as herein defined.

Such variant forms of VEGF-D can be prepared by targeting non-essential regions of the VEGF-D polypeptide for modification. These non-essential regions are expected to fall outside the strongly-conserved regions indicated in the figures herein, especially FIG. 2 and FIG. 10. In particular, the growth factors of the PDGF family, including VEGF, are dimeric, and VEGF-B, VEGF-C, PlGF, PDGF-A and PDGF-B show complete conservation of 8 cysteine residues in the N-terminal domains, ie. the PDGF-like domains (Olofsson et al, 1996; Joukov et al, 1996). These cysteines are thought to be involved in intra- and intermolecular disulphide bonding. In addition there are further strongly, but not completely, conserved cysteine residues in the C-terminal domains. Loops 1, 2 and 3 of each subunit, which are formed by intra-molecular disulphide bonding, are involved in binding to the receptors for the PDGF/VEGF family of growth factors (Andersson et al: Growth Factors, 1995 12 159–164) As shown herein, the cysteines conserved in previously known members of the VEGF family are also conserved in VEGF-D.

The person skilled in the art thus is well aware that these cysteine residues should be preserved in any proposed variant form, and that the active sites present in loops 1, 2 and 3 also should be preserved. However, other regions of the molecule can be expected to be of lesser importance for biological function, and therefore offer suitable targets for modification. Modified polypeptides can readily be tested for their ability to show the biological activity of VEGF-D by routine activity assay procedures such as cell proliferation tests.

It is contemplated that some modified VEGF-D polypeptides will have the ability to bind to endothelial cells, ie. to VEGF-D receptors, but will be unable to stimulate endothelial cell proliferation, differentiation, migration or survival. These modified polypeptides are expected to be able to act as competitive or non-competitive inhibitors of VEGF-D, and to be useful in situations where prevention or reduction of VEGF-D action is desirable. Thus such receptor-binding but non-mitogenic, non-differentiation inducing, non-migration inducing or non-survival promoting variants of VEGF-D are also within the scope of the invention, and are referred to herein as "receptor-binding but otherwise inactive variants".

According to a third aspect, the invention provides a purified and isolated nucleic acid encoding a polypeptide or polypeptide fragment of the invention. The nucleic acid may be DNA, genomic DNA, cDNA or RNA, and may be single-stranded or double stranded. The nucleic acid may be isolated from a cell or tissue source, or of recombinant or synthetic origin. Because of the degeneracy of the genetic code, the person skilled in the art will appreciate that many such coding sequences are possible, where each sequence encodes the amino acid sequence shown in SEQ ID NO:3, SEQ ID NO:5, SEQ ID NO:8 or SEQ ID NO:9, an active fragment or analogue thereof, or a receptor-binding but otherwise inactive or partially inactive variant thereof.

A fourth aspect of the invention provides vectors comprising the cDNA of the invention or a nucleic acid according to the third aspect of the invention, and host cells transformed or transfected with nucleic acids or vectors of the invention. These cells are particularly suitable for expression of the polypeptide of the invention, and include insect cells such as Sf9 cells, obtainable from the American Type Culture Collection (ATCC SRL-171), transformed with a baculovirus vector, and the human embryo kidney cell line 293EBNA transfected by a suitable expression plasmid. Preferred vectors of the invention are expression vectors in which a nucleic acid according to the invention is operatively connected to one or more appropriate promoters and/or other control sequences, such that appropriate host cells transformed or transfected with the vectors are capable of expressing the polypeptide of the invention. Other preferred vectors are those suitable for transfection of mammalian cells, or for gene therapy, such as adenovirus or retrovirus vectors or liposomes. A variety of such vectors is known in the art.

The invention also provides a method of making a vector capable of expressing a polypeptide encoded by a nucleic acid according to the invention, comprising the steps of operatively connecting the nucleic acid to one or more appropriate promoters and/or other control sequences, as described above.

The invention further provides a method of making a polypeptide according to the invention, comprising the steps of expressing a nucleic acid or vector of the invention in a host cell, and isolating the polypeptide from the host cell or from the host cell's growth medium. In one preferred embodiment of this aspect of the invention, the expression vector further comprises a sequence encoding an affinity tag, such as FLAG™ or hexahistidine, in order to facilitate purification of the polypeptide by affinity chromatography.

In yet a further aspect, the invention provides an antibody specifically reactive with a polypeptide of the invention. This aspect of the invention includes antibodies specific for the variant forms, fragments and analogues of VEGF-D referred to above. Such antibodies are useful as inhibitors or agonists of VEGF-D and as diagnostic agents for detection and quantification of VEGF-D. Polyclonal or monoclonal antibodies may be used. Monoclonal and polyclonal antibodies can be raised against polypeptides of the invention using standard methods in the art. For some purposes, for example where a monoclonal antibody is to be used to inhibit effects of VEGF-D in a clinical situation, it may be desirable to use humanized or chimeric monoclonal antibodies. Methods for producing these, including recombinant DNA methods, are also well known in the art.

This aspect of the invention also includes an antibody which recognises VEGF-D and which is suitably labelled.

Polypeptides or antibodies according to the invention may be labelled with a detectable label, and utilised for diagnostic purposes. Similarly, the thus-labelled polypeptide of the invention may be used to identify its corresponding receptor in situ. The polypeptide or antibody may be covalently or non-covalently coupled to a suitable supermagnetic, paramagnetic, electron dense, ecogenic or radioactive agent for imaging. For use in diagnostic assays, radioactive or non-radioactive labels, the latter including enzyme labels or labels of the biotin/avidin system, may be used.

Clinical applications of the invention include diagnostic applications, acceleration of angiogenesis in wound healing, tissue or organ transplantation, or to establish collateral circulation in tissue infarction or arterial stenosis, such as coronary artery disease, and inhibition of angiogenesis in the treatment of cancer or of diabetic retinopathy. Quantitation of VEGF-D in cancer biopsy specimens may be useful as an indicator of future metastatic risk.

Inasmuch as VEGF-D is highly expressed in the lung, and it also increases vascular permeability, it is relevant to a variety of lung conditions. VEGF-D assays could be used in the diagnosis of various lung disorders. VEGF-D could also be used in the treatment of lung disorders to improve blood circulation in the lung and/or gaseous exchange between the lungs and the blood stream. Similarly, VEGF-D could be used to improve blood circulation to the heart and $O_2$ gas permeability in cases of cardiac insufficiency. In like manner, VEGF-D could be used to improve blood flow and gaseous exhange in chronic obstructive airway disease.

Conversely, VEGF-D antagonists (e.g. antibodies and/or inhibitors) could be used to treat in conditions, such as congestive heart failure, involving accumulations of fluid in, for example, the lung resulting from increases in vascular permeability, by exerting an offsetting effect on vascular permeability in order to counteract the fluid accumulation.

VEGF-D is also expressed in the small intestine and colon, and administrations of VEGF-D could be used to treat malabsorptive syndromes in the intestinal tract as a result of its blood circulation increasing and vascular permeabiltiy increasing activities.

Thus the invention provides a method of stimulation of angiogenesis and/or neovascularization in a mammal in need of such treatment, comprising the step of administering an effective dose of VEGF-D, or a fragment or analogue thereof which has the ability to stimulate endothelial cell proliferation, to the mammal.

Optionally VEGF-D may be administered together with, or in conjunction with, one or more of VEGF-A, VEGF-B, VEGF-C, PlGF, PDGF, FGF and/or heparin.

Conversely the invention provides a method of inhibiting angiogenesis and/or neovascularization in a mammal in need of such treatment, comprising the step of administering an effective amount of an antagonist of VEGF-D to the mammal. The antagonist may be any agent that prevents the action of VEGF-D, either by preventing the binding of VEGF-D to its corresponding receptor or the target cell, or by preventing activation of the transducer of the signal from the receptor to its cellular site of action. Suitable antagonists include, but are not limited to, antibodies directed against VEGF-D; competitive or non-competitive inhibitors of binding of VEGF-D to the VEGF-D receptor, such as the receptor-binding but non-mitogenic VEGF-D variants referred to above; and anti-sense nucleotide sequences complementary to at least a part of the DNA sequence encoding VEGF-D.

The invention also provides a method of detecting VEGF-D in a biological sample, comprising the step of contacting the sample with a reagent capable of binding VEGF-D, and detecting the binding. Preferably the reagent capable of binding VEGF-D is an antibody directed against VEGF-D, more preferably a monoclonal antibody. In a preferred embodiment the binding and/or extent of binding is detected by means of a detectable label; suitable labels are discussed above.

Where VEGF-D or an antagonist is to be used for therapeutic purposes, the dose and route of application will depend upon the condition to be treated, and will be at the discretion of the attending physician or veterinarian. Suitable routes include subcutaneous, intramuscular or intravenous injection, topical application, implants etc. Topical application of VEGF-D may be used in a manner analogous to VEGF.

According to yet a further aspect, the invention provides diagnostic/prognostic means typically in the form of test kits. For example, in one embodiment of the invention there is provided a diagnostic/prognostic test kit comprising an antibody to VEGF-D and means for detecting, and more preferably evaluating, binding between the antibody and VEGF-D. In one preferred embodiment of the diagnostic/prognostic means according to the invention, either the antibody or the VEGF-D is labelled with a detectable label, and either the antibody or the VEGF-D is substrate-bound, such that the VEGF-D-antibody interaction can be established by determining the amount of label attached to the substrate following binding between the antibody and the VEGF-D. In a particularly preferred embodiment of the invention, the diagnostic/prognostic means may be provided as a conventional ELISA kit.

In another alternative embodiment, the diagnostic/prognostic means may comprise polymerase chain reaction means for establishing the genomic sequence structure of a VEGF-D gene of a test individual and comparing this sequence structure with that disclosed in this application in order to detect any abnormalities, with a view to establishing whether any aberrations in VEGF-D expression are related to a given disease condition.

In accordance with a further aspect, the invention relates to a method of detecting aberrations in VEGF-D gene structure in a test subject which may be associated with a disease condition in said test subject. This method comprises providing a DNA sample from said test subject; contacting the DNA sample with a set of primers specific to VEGF-D DNA operatively coupled to a polymerase and selectively amplifying VEGF-D DNA from the sample by polymerase chain reaction, and comparing the nucleotide sequence of the amplified VEGF_D DNA from the sample with the nucleotide sequences set forth in SEQ ID NO:1 or SEQ ID NO:4. The invention also includes the provision of a test kit comprising a pair of primers specific to VEGF-D DNA operatively coupled to a polymerase, whereby said polymerase is enabled to selectively amplify VEGF-D DNA from a DNA sample.

Another aspect of the invention concerns the provision of a pharmaceutical composition comprising either VEGF-D polypeptide or a fragment or analogue thereof which promotes proliferation of endothelial cells, or an antibody thereto. Compositions which comprise VEGF-D polypeptide may optionally further comprise one or more of VEGF, VEGF-B and VEGF-C, and/or heparin.

In another aspect, the invention relates to a protein dimer comprising VEGF-D polypeptide, particularly a disulphide-linked dimer. The protein dimers of the invention include both homodimers of VEGF-D polypeptide and heterodimers of VEGF-D and VEGF, VEGF-B, VEGF-C, PlGF or PDGF.

According to a yet further aspect of the invention there is provided a method for isolation of VEGF-D comprising the step of exposing a cell which expresses VEGF-D to heparin to facilitate release of VEGF-D from the cell, and purifying the thus-released VEGF-D.

Another aspect of the invention involves providing a vector comprising an anti-sense nucleotide sequence which is complementary to at least a part of a DNA sequence which encodes VEGF-D or a fragment or analogue thereof which promotes proliferation of endothelial cells. According to a yet further aspect of the invention such a vector comprising an anti-sense sequence may be used to inhibit, or at least mitigate, VEGF-D expression. The use of a vector of this type to inhibit VEGF-D expression is favoured in instances where VEGF-D expression is associated with a disease, for example where tumours produce VEGF-D in order to provide for angiogenesis. Transformation of such tumour cells with a vector containing an anti-sense nucleotide sequence would suppress or retard angiogenesis, and so would inhibit or retard growth of the tumour.

Polynucleotides of the invention such as those described above, fragments of those polynucleotides, and variants of those polynucleotides with sufficient similarity to the non-coding strand of those polynucleotides to hybridize thereto under stringent conditions all are useful for identifying, purifying, and isolating polynucleotides encoding other, non-human, mammalian forms of VEGF-D. Thus, such polynucleotide fragments and variants are intended as aspects of the invention. Exemplary stringent hybridization conditions are as follows: hybridization at 42° C. in 5×SSC, 20 mM $NaPO_4$, pH 6.8, 50% formamide; and washing at 42° C. in 0.2×SSC. Those skilled in the art understand that it is desirable to vary these conditions empirically based on the length and the GC nucleotide base content of the sequences to be hybridized, and that formulae for determining such variation exist. See for example Sambrook et al, "Molecular Cloning: A Laboratory Manual", Second Edition, Cold Spring Harbor, N.Y.: Cold Spring Harbor Laboratory (1989).

Moreover, purified and isolated polynucleotides encoding other, non-human, mammalian VEGF-D forms also are aspects of the invention, as are the polypeptides encoded thereby, and antibodies that are specifically immunoreactive with the non-human VEGF-D variants. Thus, the invention includes a purified and isolated mammalian VEGF-D polypeptide, and also a purified and isolated polynucleotide encoding such a polypeptide.

It will be clearly understood that nucleic acids and polypeptides of the invention may be prepared by synthetic means or by recombinant means, or may be purified from natural sources.

BRIEF DESCRIPTION OF THE FIGURES

FIG. 1 shows a comparison between the sequences of human VEGF-D (SEQ ID NO: 3) and human $VEGF_{165}$ (SEQ ID NO: 12) (FIG. 1A), human VEGF-D (SEQ ID NO: 3) and human VEGF-B (SEQ ID NO: 13) (FIG. 1B), human VEGF-D (SEQ ID NO: 3) and human VEGF-C (SEQ ID NO: 14) (FIG. 1C) and human VEGF-D (SEQ ID NO: 3) and human PlGF (SEQ ID NO: 15) (FIG. 1D). The box indicates residues which match those in human VEGF-D exactly;

FIG. 2 shows sequence alignments between the sequences of human VEGF-D (SEQ ID NO: 3), human $VEGF_{165}$ (SEQ ID NO: 12), human VEGF-B (SEQ ID NO: 13), human VEGF-C (SEQ ID NO: 14) and human PlGF (SEQ ID NO: 15). The boxes indicate residues that match the VEGF-D sequence exactly; and FIG. 3 shows the amino acid sequence of human VEGF-D (SEQ ID NO:3), as predicted from the cDNA sequence (SEQ ID NO:1). The boxes indicate potential sites for N-linked glycosylation.

FIG. 4 shows the nucleotide sequence of a second cDNA sequence encoding human VEGF-D (SEQ ID NO:4), isolated by hybridization from a commercial human lung cDNA library; this cDNA contains the entire coding region for human VEGF-D;

FIG. 5 shows the amino acid sequence for human VEGF-D (SEQ ID NO:5) deduced from the sequence of the cDNA of FIG. 4;

FIG. 6 shows the nucleotide sequence of cDNA encoding mouse VEGF-D1 (SEQ ID NO:6), isolated by hybridization screening for a commercially-available mouse lung cDNA library;

FIG. 7 shows the nucleotide sequence of cDNA encoding mouse VEGF-D2 (SEQ ID NO:7), isolated from the same library as in FIG. 6;

FIG. 8 shows the deduced amino acid sequences for mouse VEGF-D1 (SEQ ID NO:8) and VEGF-D2 (SEQ ID NO:9);

FIG. 9 shows a comparison between the deduced amino acid sequences of mouse VEGF-D1 (SEQ ID NO: 8), mouse VEGF-D2 (SEQ ID NO: 9) and human VEGF-D (SEQ ID NO: 5);

FIG. 10 shows sequence alignments between the amino acid sequences of human VEGF-D (SEQ ID NO: 5), human $VEGF_{165}$ (SEQ ID NO: 12), human VEGF-B (SEQ ID NO: 13), human VEGF-C (SEQ ID NO: 16) and human PlGF (SEQ ID NO: 15)

(B) Western blotting analysis of purified VEGFDΔNΔC. An aliquot of material eluted from the M2 affinity column (fraction #3, VEGFDΔNΔC) was combined with 2×SDS-PAGE sample buffer and resolved on a 15% SDS-PAGE gel. The proteins were then transferred to nitrocellulose membrane and probed with either monoclonal antibody M2 or a control isotype-matched antibody (Neg). Blots were developed using a goat anti-mouse-HRP secondary antibody and chemiluminescence (ECL , Amersham). Monomeric VEGFDΔNΔC is arrowed, as is the putative dimeric form of this peptide (VEGFDΔNΔC"). Molecular weight markers are indicated.

FIG. 13 shows the results of analysis of VEGFDΔNΔC protein using the VEGFR2 bioassay. Recombinant VEGFDΔNΔC, and material purified by M2 affinity chromatography, was assessed using the VEGFR2 bioassay. Bioassay cells ($10^4$), washed to remove IL-3, were incubated with aliquots of conditioned medium from VEGF-D transfected COS cells, fraction #1 from the affinity column (void volume) or fraction #3 from the affinity column (containing VEGFDΔNΔC). All samples were tested at an initial concentration of 20% (ie ⅕) followed by doubling dilutions. Cells were allowed to incubate for 48 hours at 37° C. in a humidified atmosphere of 10% $CO_2$. Cell proliferation was quantitated by the addition of 1 μCi of $^3$H-thymidine and counting the amount incorporated over a period of 4 hours.

Figure 14:
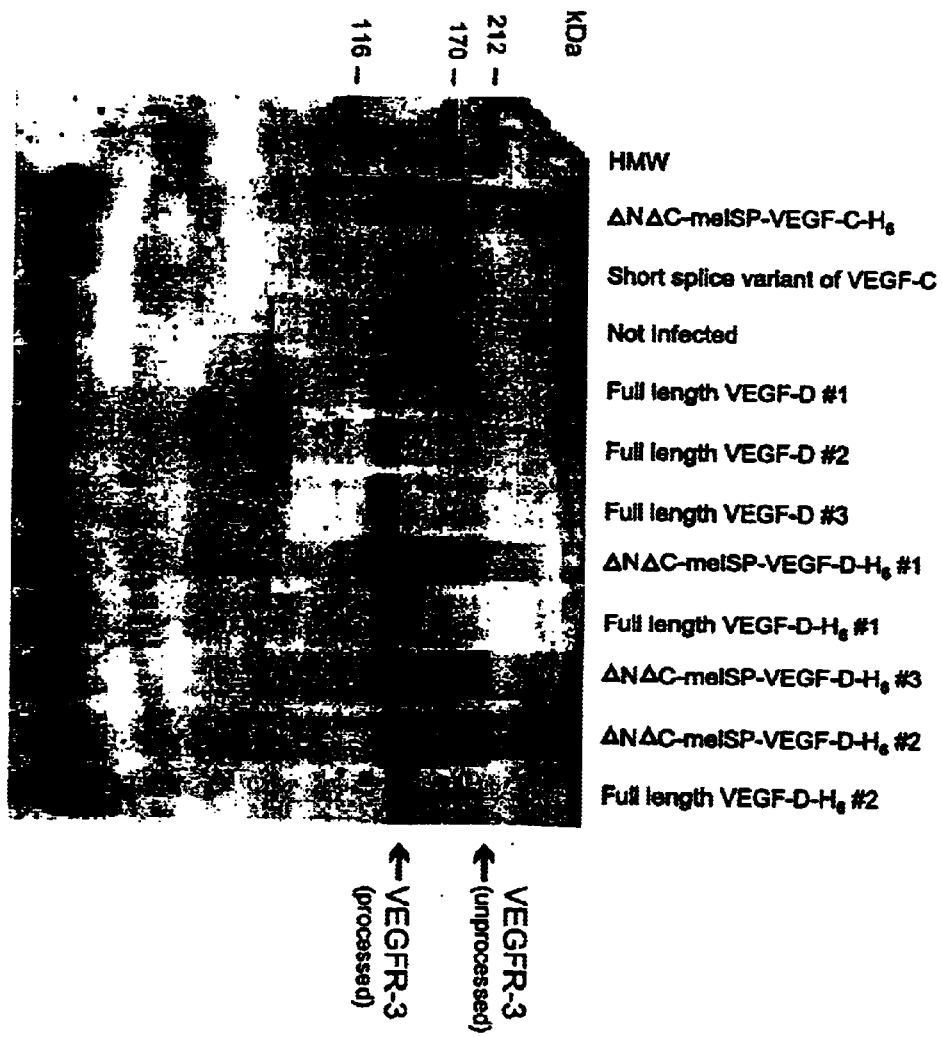

FIG. 14 shows stimulation of tyrosine phosphorylation of the VEGFR3 receptor (Flt-4) on NIH3T3 cells by culture supernatant from HF cells infected with a recombinant baculovirus vector transformed with VEGF-D.

Figure 15:
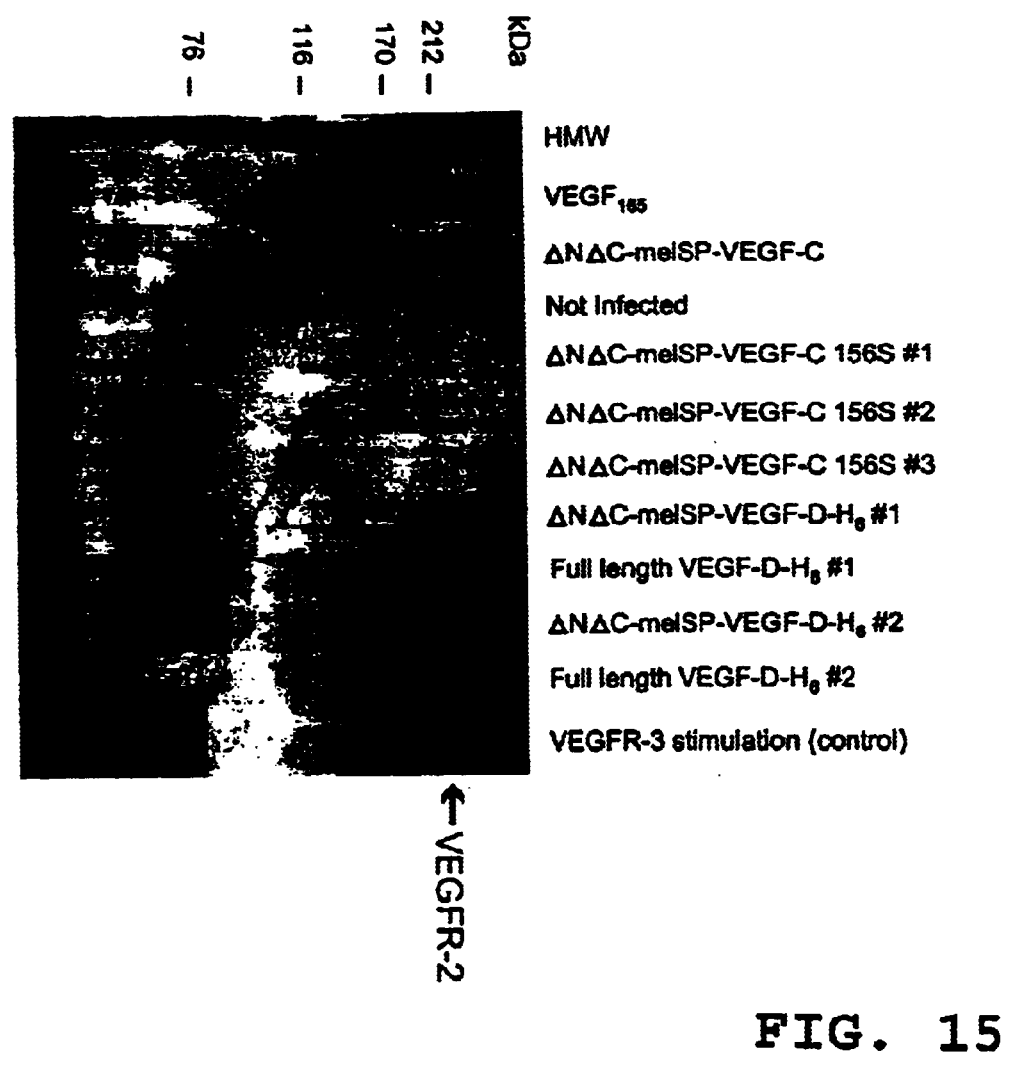

FIG. 15 shows stimulation of tyrosine phosphorylation of the VEGFR2 receptor (KDR) in PAE cells by culture supernatant prepared as in FIG. 14.

Figure 16:
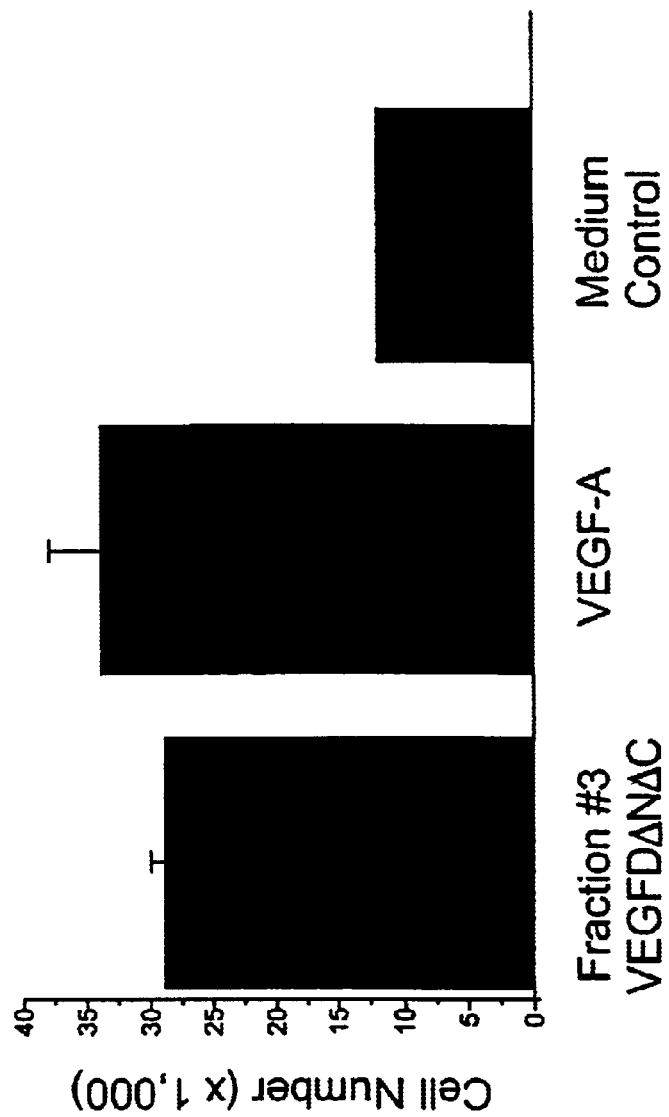

FIG. 16 shows the mitogenic effect of VEGFDΔNΔC on bovine aortic endothelial cells (BAEs). BAEs were treated with fraction #3 containing VEGFDΔNΔC and, as positive control, purified VEGF-A as described in the text. The result obtained using medium without added growth factor is denoted Medium Control.

DETAILED DESCRIPTION OF THE INVENTION

The invention will now be described in detail by reference to the figures, and to the following non-limiting examples.

EXAMPLE 1

It has been speculated that no further members of the VEGF family will be found, because there are no known orphan receptors in the VEGFR family. Furthermore, we are not aware of any suggestion in the prior art that other such family members would exist.

A computer search of nucleic acid databases was carried out incidentally to another project, using as search topics the amino acid sequences of VEGF, VEGF-B, VEGF-C and PlGF. Several cDNA sequences were identified by this search. One of these sequences, GenBank Accession No. H24828, encoded a polypeptide which was similar in structure to the cysteine-riched C-terminal region of VEGF-C. This sequence was obtained from the database of expressed sequence tags (dbEST), and for the purposes of this specification is designated XPT. The XPT cDNA had been isolated from a human cDNA library designated "Soares Breast 3NbHBst", which was constructed using mRNA from an adult human female breast tissue. As far as can be ascertained this was normal breast tissue. Sequencing of the XPT DNA was performed pursuant to the Integrated Molecular Analysis of Genome Expression Consortium (IMAGE Consortium), which solicits cDNA libraries from laboratories around the world, arrays the cDNA clones, and provides them to other organisations for sequencing.

The XPT sequence shown in the database was 419 nucleotides long, and encoded an amino acid sequence similar to the C-terminal 100 amino acids of VEGF-C, ie. approximately residues 250 to 350, using the numbering system of Joukov et al (1996). Similarly cysteine-rich regions are found in other proteins, which are entirely unrelated in function to the VEGF family, for example the secreted silk-like protein sp185 synthesized in the salivary glands of the midge Chironomus tentans. This protein is encoded by the gene BR3, located in a Balbiani ring, a tissue specific chromosome "puff" found on polytene chromosomes in the midge salivary gland (Dignam and Case: Gene, 1990 88 133–140; Paulsson et al, J. Mol. Biol., 1990 211 331–349). It is stated in Joukov et al (1996) that the sp185-like structural motif in VEGF-C may fold into an independent domain, which is thought to be at least partially cleaved off after biosynthesis, and that there is at least one cysteine motif of the sp185 type in the C-terminal region of VEGF.

FIG. 3 of Joukov et al shows that the last two-thirds of the C-terminal cysteine-rich region of VEGF-C do not align with VEGF or PlGF, and in fact could be considered a C-terminal extension of VEGF-C which is not present in VEGF or PlGF. The sequence encoded by XPT is similar to this extension. As the XPT cDNA was truncated at its 5' end, it was not possible to deduce or predict any amino acid sequence for regions N-terminal to the cysteine-rich domain. Thus the portion of VEGF-C which is similar to the XPT-derived sequence does not extend to regions of VEGF-C which are conserved among other members of the VEGF family.

As described above, it was not possible to predict whether the N-terminal region of the polypeptide encoded by a full-length XPT nucleic acid (as distinct from the truncated XPT cDNA reported in dbEST) would show any further homology to any member of the VEGF family, in particular VEGF-C, which has a further N-terminal 250 amino acids. For example, the naturally-occurring protein encoded by a full-length XPT nucleic acid could have been the human homologue of the midge salivary gland protein. Alternatively, the type of cysteine-rich motif encoded by truncated XPT cDNA could be widely distributed among proteins, as are many structural domains. For example, clusters of cysteine residues may be involved in metal binding, formation of intramolecular disulphide bonds to promote accurate protein folding, or formation of intermolecular disulphide bonds for assembly of protein subunits into complexes (Dignam and Chase, 1990). In order to determine whether the truncated XPT cDNA was derived from sequences encoding a VEGF-related molecule, it was necessary to isolate a much longer cDNA.

EXAMPLE 2

Cloning of cDNA Encoding VEGF-D

A sample of the XPT cDNA reported in dbEST was obtained from the American Type Culture Collection, which is a registered supplier of cDNA clones obtained by the IMAGE Consortium. The identity of the XPT cDNA was confirmed by nucleotide sequencing, using the dideoxy chain termination method (Sanger et al, Proc. Natl. Acad. Sci. USA, 1977 74 5463–5467).

The XPT cDNA was used as a hybridization probe to screen a human breast cDNA library, which was obtained commercially from Clontech. One positive clone was isolated, and this clone was then sequenced on both strands. The nucleotide sequence was compiled, and an open reading frame was identified. The nucleic acid sequence is set out in SEQ ID NO:1. The polypeptide encoded by this sequence was designated VEGF-D, and its deduced amino acid sequence, designated SEQ ID NO:3, is set out in FIG. 3. In FIG. 3 putative sites of N-linked glycosylation, with the consensus sequence N-X-S/T in which X is any amino acid, are indicated by the boxes.

EXAMPLE 3

Characteristics of VEGF-D

The amino acid sequence of VEGF-D was compared with those of human VEGF-$A_{165}$, VEGF-B, VEGF-C and PlGF. These comparisons are set out in FIGS. 1A to D, respectively. The degree of sequence homology was calculated, and if gaps in sequence introduced for the purposes of alignment are not considered in the calculation, VEGF-D is 31% identical to VEGF, 48% identical to VEGF-C, 28% identical to VEGF-B and 32% identical to PlGF. Thus the most closely-related protein identified was VEGF-C.

Computer searches of the GenBank, EMBL and SwissProt nucleic acid databases did not reveal any protein sequences identical to VEGF-D. As expected from the sequence alignment referred to above, the most closely related protein found in these databases was VEGF-C. Searches of dbEST were also performed, but did not reveal any sequences encompassing the entire coding region of VEGF-D. The sequence of VEGF-D is unrelated to that of Tie-2 ligand 1 as disclosed in WO 96/11269.

It is important to bear in mind that the only homologies detected were at the level of amino acid sequence. Thus it would not have been possible to isolate the cDNA or gDNA encoding VEGF-D by methods such as low-stringency hybridization with a nucleic acid sequence encoding another member of the VEGF family.

VEGF-D appears to be most closely related to VEGF-C of all the members of the VEGF family. Because the VEGF-D amino acid sequence includes the cysteine-rich sp185-like motif which is found in VEGF-C, the polypeptide of the invention may play an important functional role in lymphatic endothelia. While we do not wish to be bound by any proposed mechanism, it is thought that VEGF-C and VEGF-D may constitute a silk-like matrix over which endothelial cells can grow. Lymphatic vessels have no basement membrane, so the silk-like matrix can form a basement membrane-like material. This may be important in promoting cell growth and/or in cell differentiation, and may be relevant to cancer, especially metastasis, drug therapy, cancer prognosis, etc.

EXAMPLE 4

Biological Characteristics of VEGF-D

The cDNA sequence of VEGF-D was used to predict the deduced amino acid sequence of VEGF-D, the biochemical characteristics of the encoded polypeptide, including the numbers of strongly basic, strongly acidic, hydrophobic and polar amino acids, the molecular weight, the isoelectric point, the charge at pH 7, and the compositional analysis of the whole protein. This analysis was performed using the Protean protein analysis program, Version 1.20 (DATASTAR). These results are summarised in Tables 1 and 2 below. Table 1 also shows the codon usage.

TABLE 1

Translated DNA Sequence of VEGF-D contig x(1,978)
With Standard Genetic Code

Molecular Weight 37056.60 Daltons
425 Amino Acids
46 Strong Basic(+) Amino Acids (K,R)
41 Strong Acidic(−) Amino Acids (D,E)
79 hydrophobic Amino Acids (A,I,L,F,W,V)

TABLE 1-continued

Translated DNA Sequence of VEGF-D contig x(1,978)
With Standard Genetic Code

108 Polar Amino Acids (N,C,Q,S,T,Y)
7.792 Isoelectric Point
6.371 Charge at pH 7.0
Total number of bases translated is 978
% A = 28.73 [281]
% G = 23.11 [226]
% T = 23.21 [227]
% C = 24.95 [244]
% Ambiguous = 0.00 [0]
% A + T = 51.94 [508]
% C + G = 48.06 [470]
Davis, Botstein, Roth Melting Temp ° C. 84.09
Wallace Temp ° C. 3384.00

Codon usage:

| | | | | |
|---|---|---|---|---|
| ccg ( ) | 0 # ugc Cys(C) | 14 # cuc Leu(L) | 6 # ucg Ser(S) | |
| uaa ( ) | 0 # ugu Cys(C) | 16 # cug Leu(L) | 4 # ucu Ser(S) | |
| uag ( ) | 0 # --- Cys(C) | 30 # cuu Leu(L) | 2 # --- Ser(S) | 3 |
| --- ( ) | 0 # caa Gln(Q) | 1 # uua Leu(L) | 1 # uga Ter(.) | |
| gca Ala(A) | 5 # cag Gln(Q) | 11 # uug Leu(L) | 5 # --- Ter(.) | |
| gcc Ala(A) | 4 # --- Gln(Q) | 12 # --- Leu(L) | 23 # aca Thr(T) | |
| gcg Ala(A) | 1 # gaa Glu(E) | 16 # aaa Lys(K) | 13 # acc Thr(T) | |
| gcu Ala(A) | 5 # gag Glu(E) | 12 # aag Lys(K) | 10 # acg Thr(T) | |
| --- Ala(A) | 15 # --- Glu(E) | 28 # --- Lys(K) | 23 # acu Thr(T) | |
| aga Arg(R) | 7 # gga Gly(G) | 1 # aug Met(M) | 6 # --- Thr(T) | 2 |
| agg Arg(R) | 5 # ggc Gly(G) | 2 # --- Met(M) | 6 # ugg Trp(W) | |
| cga Arg(R) | 5 # ggg Gly(G) | 3 # uuc Phe(F) | 4 # --- Trp(W) | |
| cgc Arg(R) | 4 # ggu Gly(G) | 2 # uuu Phe(F) | 8 # uac Tyr(Y) | |
| cgg Arg(R) | 1 # --- Gly(G) | 8 # --- Phe(F) | 12 # uau Tyr(Y) | |
| cgu Arg(R) | 1 # cac His(H) | 7 # cca Pro(P) | 9 # --- Tyr(Y) | |
| --- Arg(R) | 23 # cau His(H) | 7 # ccc Pro(P) | 6 # gua Val(V) | |
| aac Asn(N) | 5 # --- His(H) | 14 # ccu Pro(P) | 8 # guc Val(V) | |
| aau Asn(N) | 4 # aua Ile(I) | 2 # --- Pro(P) | 23 # gug Val(V) | |
| --- Asn(N) | 9 # auc Ile(I) | 6 # agc Ser(S) | 6 # guu Val(V) | |
| gac Asp(D) | 8 # auu Ile(I) | 5 # agu Ser(S) | 8 # --- Val(V) | 1 |
| gau Asp(D) | 5 # --- Ile(I) | 13 # uca Ser(S) | 5 # nnn ??? (X) | |
| gau Asp(D) | 5 # --- Ile(I) | 13 # uca Ser(S) | 5 # nnn ??? (X) | |
| --- Asp(D) | 13 # cua Leu(L) | 5 # ucc Ser(S) | 7 # TOTAL | 32 |

Contig 2:

| | |
|---|---|
| Contig Length: | 2379 bases |
| Average Length/Sequence: | 354 bases |
| Total Sequence Length: | 4969 bases |

TABLE 2

Predicted Structural Class of the Whole Protein:
Deléage & Roux Modification of Nishikawa & Ooi 1987

| Analysis | Whole Protein |
|---|---|
| Molecular Weight | 37056.60 m.w. |
| Length | 325 |
| 1 microgram = | 26.986 pMoles |
| Molar Extinction coefficient | 30200 ± 5% |
| 1 A(280) = | 1.23 mg/ml |
| Isoelectric Point | 7.79 |
| Charge at pH 7 | 6.37 |

Whole Protein Composition [Anayalsis] Analysis

| Amino Acid(s) | Number count | % by weight | % by frequency |
|---|---|---|---|
| Charged (RKHYCDE) | 134 | 46.30 | 41.23 |
| Acidic (DE) | 41 | 13.79 | 12.62 |
| Basic (KR) | 46 | 17.65 | 14.15 |
| Polar (NCQSTY) | 108 | 30.08 | 33.23 |
| Hydrophobic (AILFWV) | 79 | 23.86 | 24.31 |
| A Ala | 15 | 2.88 | 4.62 |
| C Cys | 30 | 8.35 | 9.23 |
| D Asp | 13 | 4.04 | 4.00 |
| E Glu | 28 | 9.75 | 8.62 |
| F Phe | 12 | 4.77 | 3.69 |
| G Gly | 8 | 1.23 | 2.46 |
| H His | 14 | 5.18 | 4.31 |
| I Ile | 13 | 3.97 | 4.00 |
| K Lys | 23 | 7.96 | 7.08 |
| L Leu | 23 | 7.03 | 7.08 |
| M Met | 6 | 2.12 | 1.85 |
| N Asn | 9 | 2.77 | 2.77 |
| P Pro | 23 | 6.08 | 7.08 |
| Q Gln | 12 | 4.15 | 3.69 |
| R Arg | 23 | 9.69 | 7.08 |
| S Ser | 33 | 7.76 | 10.15 |
| T Thr | 21 | 5.73 | 6.46 |
| V Val | 12 | 3.21 | 3.69 |
| W Trp | 4 | 2.01 | 1.23 |
| Y Trp | 3 | 1.32 | 0.92 |
| B Asx | 0 | 0.00 | 0.00 |
| Z Glx | 0 | 0.00 | 0.00 |
| X Xxx | 0 | 0.00 | 0.00 |
| . Ter | 0 | 0.00 | 0.00 |

This analysis predicts a molecular weight for the unprocessed VEGF-D monomer of 37 kilodaltons (kD), compared to the experimentally determined values (for the fully processes peptides) of 20 to 27 kD for VEGF-A monomers, 21 kD for the VEGF-B monomer and 23 kD for the VEGF-C monomer.

EXAMPLE 5

The original isolation of a cDNA for VEGF-D, described in Example 2 involved hybridization screening of a human breast cDNA library. As only one cDNA clone for VEGF-D was thus isolated, it was not possible to confirm the structure of the cDNA by comparison with other independently isolated VEGF-D cDNAs. The work described in this example, which involved isolation of additional human VEGF-D cDNA clones, was carried out in order to confirm the structure of human VEGF-D cDNA. In addition, mouse VEGF-D cDNA clones were isolated.

Two cDNA libraries which had been obtained commercially from Stratagene, one for human lung and one for mouse lung (catalogue numbers 937210 and 936307, respectively) were used for hybridization screening with a VEGF-D cDNA probe. The probe, which spanned from nucleotides 1817 to 2495 of the cDNA for human VEGF-D described in Example 2, was generated by polymerase chain reaction (PCR) using a plasmid containing the VEGF-D cDNA as template and the following two oligonucleotides:

5'-GGGCTGCTTCTAGTTTGGAG (SEQ ID NO:10), and

5'-CACTCGCAACGATCTTCGTC (SEQ ID NO:1).

Approximately two million recombinant bacteriophage were screened with this probe from each of the two cDNA libraries. Nine human and six mouse cDNA clones for VEGF-D were subsequently isolated.

Two of the nine human cDNA clones for VEGF-D were sequenced completely using the dideoxy chain termination method (Sanger et al, Proc. Natl. Acad. Sci. USA, 1977 74 5463–5467). The two cDNAs contained the entire coding region for human VEGF-D, and were identical except that one of the clones was five nucleotides longer than the other at the 5'-terminus. The nucleotide sequence of the shorter cDNA is shown in FIG. 4, and is designated SEQ ID NO:4. The amino acid sequence for human VEGF-D (hVEGF-D) deduced from this cDNA was 354 residues long, and is shown in FIG. 5; this is designated SEQ ID NO:5. The sequences of the 5' regions of five of the other human VEGF-D cDNA clones were also determined. For each clone, the sequence that was characterized contained more than 100 nucleotides of DNA immediately downstream from the translation start site of the coding region. In all cases, the sequences of these regions were identical to corresponding regions of the human VEGF-D cDNA shown in FIG. 4.

All six mouse cDNA clones for VEGF-D were sequenced completely. Only two of the clones contained an entire coding region for VEGF-D; the other clones were truncated. The nucleotide sequences of the two clones with an entire coding region are different, and encode amino acid sequences of different sizes. The longer amino acid sequence is designated mVEGF-D1, and the shorter sequence is designated mVEGF-D2. The nucleotide sequences of the cDNAs encoding mVEGF-D1 and mVEGF-D2 are shown in FIGS. 6 and 7 respectively. The deduced amino acid sequences for mVEGF-D1 and mVEGF-D2 are shown in FIG. 8. These sequences are respectively designated SEQ ID NOS. 6, 7, 8 and 9. The differences between the amino acid sequences are:

i) an insertion of five amino acids (DFSFE) residues 31-35 of SEQ ID NO: 8) after residue 30 in mVEGF-D1 in comparison to mVEGF-D2;

ii) complete divergence of the C-terminal ends after residue 317 in mVEGF-D1 and residue 312 in mVEGF-D2, which results in mVEGF-D1 being considerably longer.

Three of the four truncated cDNAs for mouse VEGF-D encoded the C-terminal region, but not the N-terminal 50 amino acids. All three of these cDNAs encoded a C-terminal end for VEGF-D which is identical to that for mVEGF-D2. The other truncated cDNA encoded only the N-terminal half of VEGF-D. The amino acid sequence deduced from this cDNA contained the five amino acids DFSFE (residues 31-35 of SEQ ID NO: 8) immediately after residue 30 found in mVEGF-D1, but not in mVEGF-D2.

As described above, the entire sequence of the human VEGF-D cDNA clone reported in this example has been validated by comparison with that for a second human clone. In addition, the sequence of the 5' end of the coding region was found to be identical in five other human VEGF-D cDNA clones. In contrast, the sequence reported in Example 2 contained most of the coding region for VEGF-D, but was incorrect near the 5'-end of this region. This was probably because the VEGF-D cDNA was truncated near the 5'-end of the coding region and at that point had been ligated with another unidentified cDNA, and consequently the first 30 codons of the true coding sequence for VEGF-D had been deleted and replaced with a methionine residue. This methionine residue was defined as the N-terminal amino acid of the VEGF-D sequence presented in Example 2.

Figure 9:
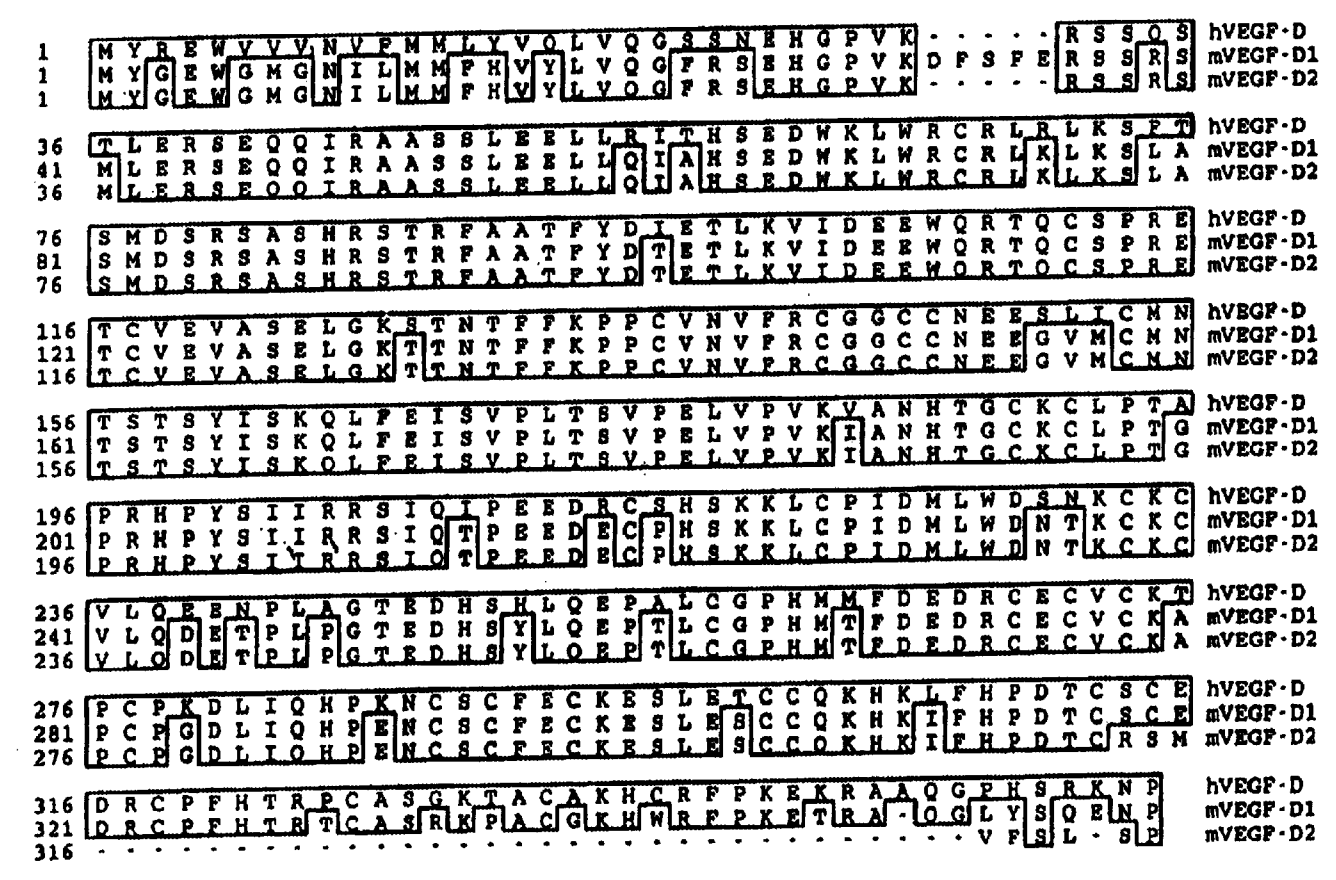
Figure 10:
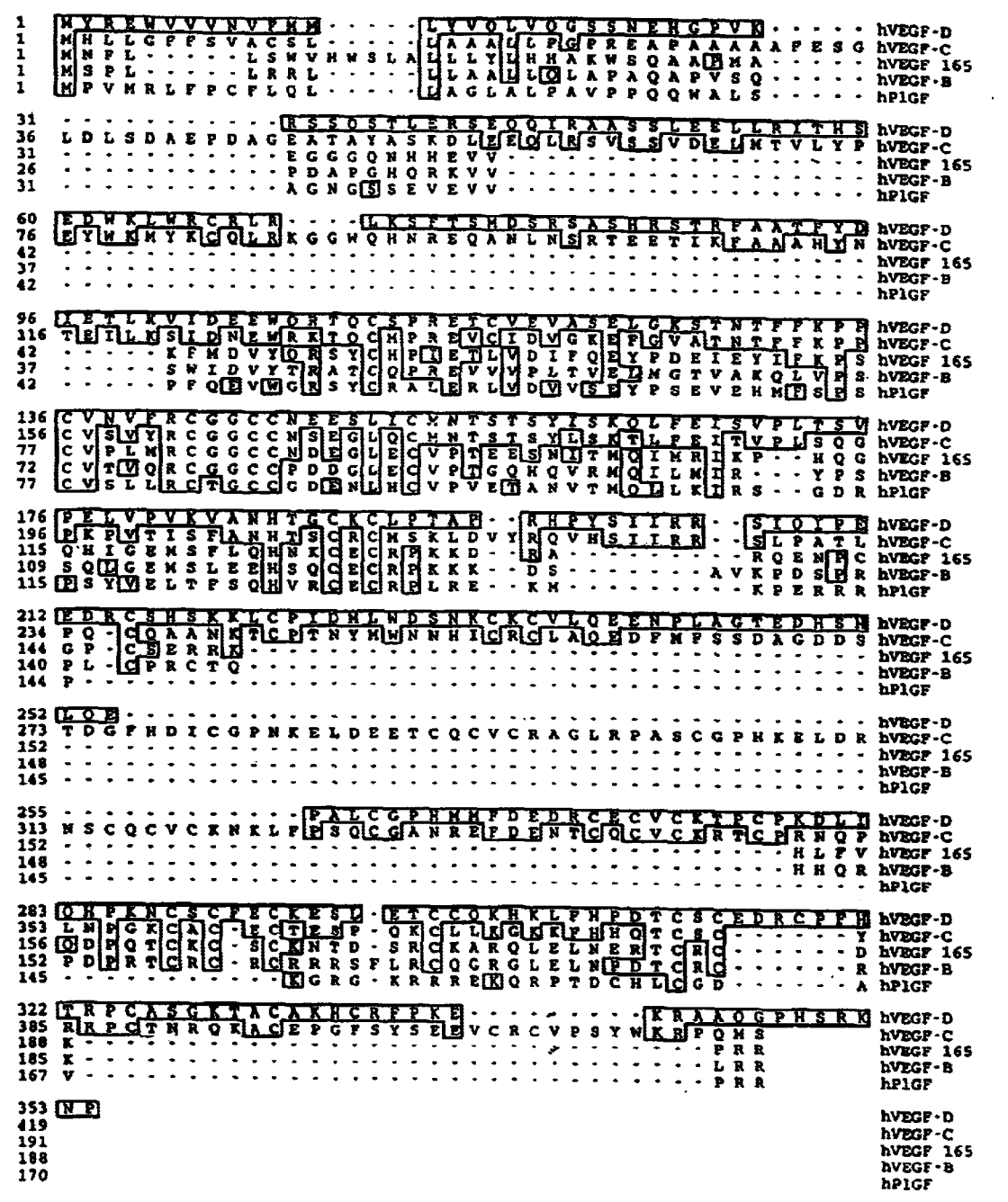

The N-terminal regions of the deduced amino acid sequences of mouse VEGF-D1 and VEGF-D2 are very similar to that deduced for human VEGF-D (see FIG. 9). This also indicates that the correct deduced amino acid sequence for human VEGF-D is reported in this example. The N-terminal 25 amino acids of human VEGF-D form an extremely hydrophobic region, which is consistent with the notion that part of this region may be a signal sequence for protein secretion. FIG. 10 shows the alignment of the human VEGF-D sequence with the sequences of other members of the VEGF family of growth factors, namely human $VEGF_{165}$ ($hVEGF_{165}$), human VEGF-B (hVEGF-B), human VEGF-C (hVEGF-C) and human Placental Growth Factor (hPlGF). When gaps in the alignments are ignored for the purposes of calculation, human VEGF-D is found to be 31% identical in amino acid sequence to human $VEGF_{165}$, 28% identical to human VEGF-B, 48% identical to VEGF-C and 32% identical to human PlGF. Clearly VEGF-C is the member of this family which is most closely related to VEGF-D.

The differences in sequence for mouse VEGF-D1 and VEGF-D2 most probably arise from differential mRNA splicing. The C-terminal 41 amino acid residues of VEGF-D1 are deleted in VEGF-D2, and are replaced with 9 residues which are not closely related to the VEGF-D1 sequence. Therefore 4 cysteine residues present near the C-terminus of VEGF-D1 are deleted in VEGF-D2. This change may alter the tertiary or quaternary structures of the protein, or may affect the localisation of the protein in the cell or the extracellular environment. The C-terminal end of human VEGF-D resembles that of mouse VEGF-D1, not mouse VEGF-D2. The small 5 amino acid insertion after residue 30 in mouse VEGF-D1, which is not present in either mouse VEGF-D2 or human VEGF-D, may influence proteolytic processing of the protein.

VEGF-D is highly conserved between mouse and man. Eighty-five percent of the amino acid residues of human VEGF-D are identical in mouse VEGF-D1. This is likely to reflect conservation of protein function. Putative functions for VEGF-D have been proposed herein. Although we have not found alternative forms of human VEGF-D cDNA, it is possible that the RNA splice variation which gives rise to numerous forms of mRNA for mouse VEGF-D may also occur in human tissues.

EXAMPLE 6

Expression of VEGF-D in COS Cells

A fragment of the human cDNA for VEGF-D, spanning from nucleotide 1 to 1520 of the sequence shown in FIG. 4 and containing the entire coding region, was inserted into the mammalian expression vector pcDNA1-amp. The vector was used to transiently transfect COS cells by the DEAE-Dextran method as described previously (Aruffo and Seed, 1987) and the resulting conditioned cell culture media, collected after 7 days of incubation, were concentrated using Amicon concentrators (Centricon 10 with a 10,000 molecular weight cut off) according to the manufacturer. The plasmids used for transfections were the expression construct for human VEGF-D and, as positive control, a construct made by insertion of mouse VEGF-A cDNA into pcDNA1-amp. The conditioned media were tested in two different bioassays, as described below, and the results demonstrate that the COS cells did in fact express and secrete biologically-active VEGF-D.

EXAMPLE 7

Bioassay for Capacity of VEGF-D to Bind to VEGF Receptor-2

As shown in Example 5, VEGF-D is closely related in primary structure to other members of the VEGF family. Most members of this protein family are mitogenic and/or chemotactic for endothelial cells (Keck et al, 1989; Leung et al, 1989; Joukov, et al, 1996; Olofsson et al, 1996). In addition VEGF-A (previously known as VEGF), the first member of the VEGF family to be described in the literature, is a potent inducer of vascular permeability (Keck et al, 1989). As protein structure is an important determinant of protein function, it seemed likely that VEGF-D might also be mitogenic for endothelial cells or induce vascular permeability. Therefore human VEGF-D was tested in a bioassay for its capacity to bind to VEGF receptor-2 (VEGFR2; also known as Flk-1), an endothelial cell-specific receptor which, when activated by VEGF-A, is thought to give rise to a mitogenic signal (Strawn et al, 1996).

A bioassay for detection of growth factors which bind to VEGFR2 has been developed in the factor-dependent cell line Ba/F3, and is described in our earlier patent application, No. PCT/US95/16755. These cells grow in the presence of interleukin-3 (IL-3); however removal of this factor results in cell death within 48 hours. If another receptor capable of delivering a growth stimulus is transfected into the Ba/F3 cells, the cells can be rescued by the specific growth factor which activates that receptor when the cells are grown in medium lacking IL-3. In the specific case of receptor-type tyrosine kinases (eg. VEGFR2), chimeric receptors containing the extracellular domain of the receptor tyrosine kinase and the transmembrane and cytoplasmic domains of the erythropoietin receptor (EpoR) can be utilised. In this case stimulation with the ligand (eg. VEGF), which binds to the extracellular domain of the chimeric receptor, results in signalling via the EpoR cytoplasmic domain and subsequent rescue of the cell line in growth medium lacking IL-3. The construction of the chimeric receptor used in this study, consisting of the mouse VEGFR2 extracellular domain and the mouse EpoR transmembrane and cytoplasmic domains, and the bioassay itself are described below.

Plasmid Construction i) Construction of a Plasmid for Generating Chimeric VEGFR2 Receptors To obtain a plasmid construct with which DNA encoding the extracellular domain of mouse VEGFR2 could easily be ligated with DNA encoding other protein domains, site-directed mutagenesis was used to generate a BglII restriction enzyme site at the position of mouse VEGFR2 cDNA which encoded the junction of the extracellular domain and the transmembrane domain. The full-length clone of the mouse VEGFR2 cDNA described by Oelrichs et al (1993) was subcloned into the mammalian expression vector pcDNA1-amp, using the BstXI restriction enzyme site. Single stranded UTP+ DNA was generated using the M13 origin of replication, and this was used as a template to generate mouse VEGFR2 cDNA containing the BglII site at the desired position. The plasmid containing the altered VEGFR2 cDNA was designated pVEGFR2Bgl. DNA fragments encoding the transmembrane and cytoplasmic domains of any receptor can be inserted at the BglII site of pVEGFR2Bgl in order to generate chimeric VEGFR2 receptors.

ii) Construction of VEGFR2/EpoR Chimeric Receptor

The mouse EpoR cDNA was subcloned into the expression vector pcDNA1-amp, and single stranded DNA was generated as a template for mutagenesis. A BglII restriction enzyme site was inserted into the EpoR cDNA at the position encoding the junction of the transmembrane and extracellular domains of the EpoR to allow direct ligation of this DNA fragment to the modified cDNA encoding the extracellular domain of VEGFR2 in pVEGFR2Bgl. In addition a BglII site in the cytoplasmic domain of the EpoR was removed by a silent single nucleotide substitution. The DNA fragment encoding the transmembrane and cytoplasmic domains of EpoR was then used to replace the portion of pVEGFR2Bgl encoding the transmembrane and cytoplasmic domains of VEGFR2. Thus a single reading frame was generated which encoded the chimeric receptor consisting of the VEGFR2 extracellular domain and the EpoR transmembrane and cytoplasmic domains.

The DNA fragment encoding the chimeric receptor was subcloned into the expression vector pBOS, and co-transfected into the Ba/F3 cell line with plasmid pgk-neo at a ratio of 1:20. Cells expressing the VEGFR2-EpoR protein were selected by flow cytometry analysis using a monoclonal antibody to the VEGFR2 extracellular domain (MAb 4H3). This monoclonal antibody is described in Australian Patent Application No. PM 3794 filed Feb. 10, 1994. Cell lines expressing higher levels of VEGFR2-EpoR were selected by growing the cells in 5 $\mu$g/ml MAb 4H3 or 25 ng/ml of recombinant VEGF. A cell line expressing high levels of VEGFR2-EpoR, designated Ba/F3-NYK-EpoR, was used for the bioassay.

The Bioassay

The Ba/F3-NYK-EpoR cells described above were washed three times in PBS to remove all IL-3 and resuspended at a concentration of 1000 cells per 13.5 $\mu$l of culture medium and 13.5 $\mu$l was aliquoted per well of a 60-well Terasaki plate. Conditioned media from transfected COS cells were then diluted into the cell culture medium. Cells expressing a chimeric receptor consisting of the extracellular domain of the endothelial cell receptor Tie2 and the transmembrane and cytoplasmic domains of EpoR were used as a non-responding control cell line. Cells were incubated for 48–96 hours, during which the cells incubated in cell culture medium alone had died and the relative survival/proliferation seen in the other wells (ie. in the presence of COS cell-conditioned media) was scored by counting the viable cells present per well.

The conditioned medium from COS cells which had been transiently transfected with expression plasmids was concentrated 30-fold and used in the VEGFR2 bioassay. Concentrated conditioned medium from COS cells transfected with pcDNA1-amp was used as negative control.

Figure 11:
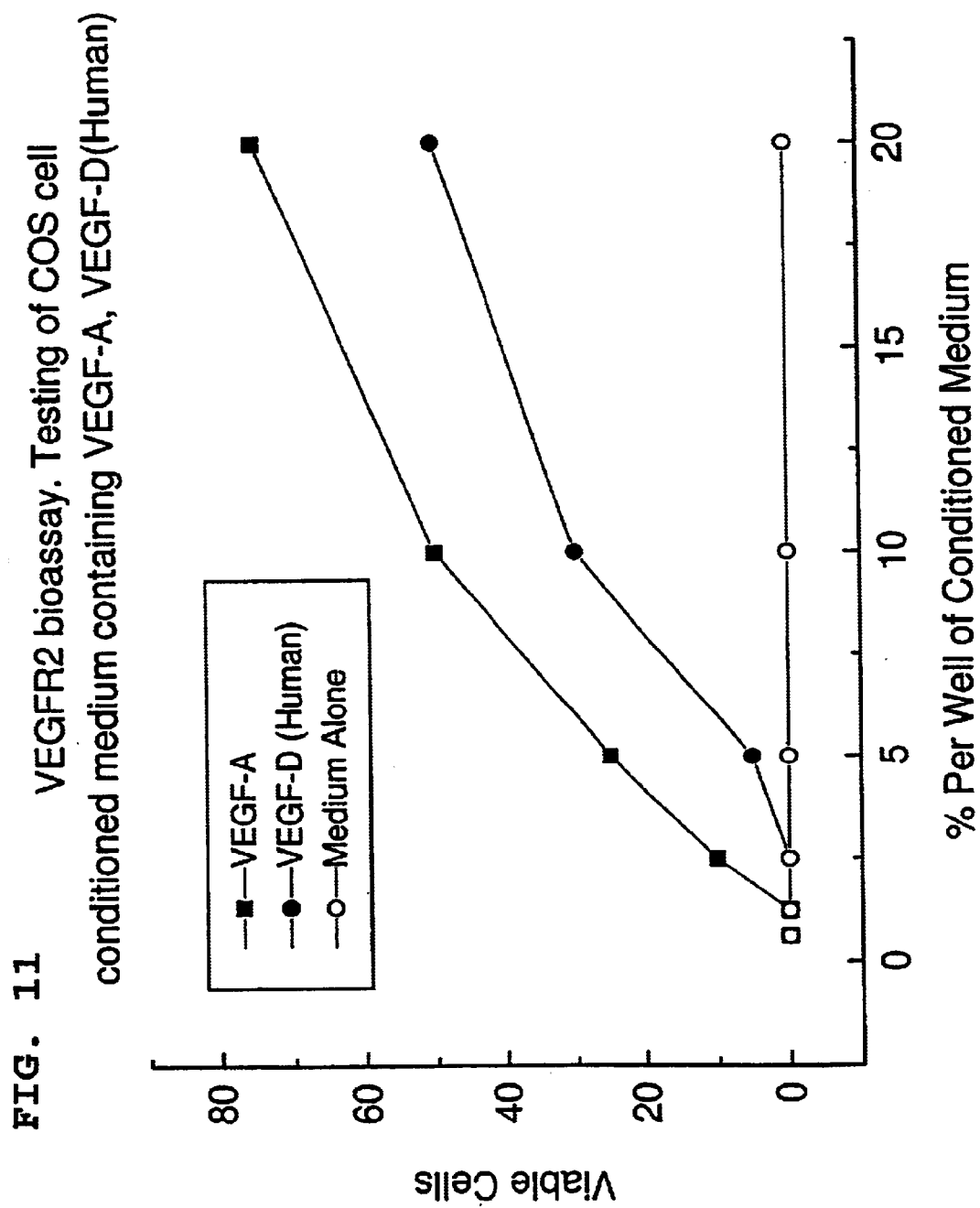
FIG. 11 shows the results of a bioassay in which conditioned medium from COS cells expressing either VEGF-A or VEGF-D was tested for ability to bind to the extracellular domain of a chimeric receptor expressed in Ba/F3 cells.

The results are shown in FIG. 11, with the percentage of 30-fold concentrated COS cell-conditioned medium in the incubation medium (vol/vol) plotted versus the number of viable cells in the well after 48 hours of incubation. Clearly the conditioned medium containing either VEGF-A or VEGF-D was capable of promoting cell survival in this assay, indicating that both proteins can bind to and activate VEGFR2.

EXAMPLE 8

Vascular Permeability Assay

Human VEGF-D, prepared as in Example 6 and concentrated 30-fold, was tested in the Miles vascular permeability assay (Miles and Miles, 1952) performed in anaesthetized guinea pigs (albino/white, 300–400 g). Concentrated conditioned medium for COS cells transfected with pcDNA1-amp was again used as a negative control. Guinea pigs were anaesthetised with chloral-hydrate (3.6 g/100 ml; 0.1 ml per 10 g of body weight). The backs of the animals were then carefully shaved with clippers. Animals were given an intracardiac injection of Evans Blue dye (0.5% in MT PBS, 0.5 ml) using a 23 G needle, and were then injected intra-dermally with 100–150 µl of concentrated COS cell-conditioned medium. After 15–20 min the animals were sacrificed and the layer of skin on the back excised to expose the underlying blood vessels. For quantitation, the area of each injection was excised and heated to 45° C. in 2–5 ml of formamide. The resulting supernatants, containing extravasated dye, were then examined spectrophotometrically at 620 nm.

For animal 1, the absorbance at 620 nm arising from injection of 30-fold concentrated VEGF-A conditioned medium was 0.178, that for the 30-fold concentrated VEGF-D conditioned medium was 0.114, and that for 30-fold concentrated medium from cells transfected with pcDNA1-amp was 0.004. For animal 2, the 30-fold concentrated media were diluted 4-fold in cell culture medium before intra-dermal injection. The absorbance at 620 nm for the VEGF-A conditioned sample was 0.141, that for the VEGF-D conditioned sample was 0.116 and that for a sample matched for serum content as negative control was 0.017. The enhanced extravasation of dye observed for both animals in the presence of VEGF-A or VEGF-D demonstrated that both of these proteins strongly induced vascular permeability.

The data described here indicate that VEGF-D is a secreted protein which, like VEGF-A, binds to and activates VEGFR2 and can induce vascular permeability.

EXAMPLE 9

Bioactivities of Internal VEGF-D Polypeptides

The deduced amino acid sequence for VEGF-D includes a central region which is similar in sequence to all other members of the VEGF family (approximately residues 101 to 196 of the human VEGF-D amino acid sequence as shown in the alignment in FIG. 10). Therefore, it was thought that the bioactive portion of VEGF-D might reside in the conserved region. In order to test this hypothesis, the biosynthesis of VEGF-D was studied, and the conserved region of human VEGF-D was expressed in mammalian cells, purified, and tested in bioassays as described below.

Plasmid Construction

A DNA fragment encoding the portion of human VEGF-D from residue 93 to 201, ie. with N- and C-terminal regions removed, was amplified by polymerase chain reaction with Pfu DNA polymerase, using as template a plasmid comprising full-length human VEGF-D cDNA. The amplified DNA fragment, the sequence of which was confirmed by nucleotide sequencing, was then inserted into the expression vector pEFBOSSFLAG to give rise to a plasmid designated pEFBOSVEGFDΔNΔC. The pEFBOSSFLAG vector contains DNA encoding the signal sequence for protein secretion from the interleukin-3 (IL-3) gene and the FLAG™ octapeptide. The FLAG™ octapeptide can be recognized by commercially available antibodies such as the M2 monoclonal antibody (IBI/Kodak). The VEGF-D PCR fragment was inserted into the vector such that the IL-3 signal sequence was immediately upstream from the FLAG™ sequence, which was in turn immediately upstream from the VEGF-D sequence. All three sequences were in the same reading frame, so that translation of mRNA resulting from transfection of pEFBOSVEGFDΔNΔC into mammalian cells would give rise to a protein which would have the IL-3 signal sequence at its N-terminus, followed by the FLAG™ octapeptide and the VEGF-D sequence. Cleavage of the signal sequence and subsequent secretion of the protein from the cell would give rise to a VEGF-D polypeptide which is tagged with the FLAG™ octapeptide adjacent to the N-terminus. This protein was designated VEGFDΔNΔC.

In addition, a second plasmid was constructed, designated pEFBOSVEGFDfullFLAG, in which the full-length coding sequence of human VEGF-D was inserted into pEFBOSI-FLAG such that the sequence for the FLAG™ octapeptide was immediately downstream from, and in the same reading frame as, the coding sequence of VEGF-D. The plasmid pEFBOSIFLAG lacks the IL-3 signal sequence, so secretion of the VEGF-D/FLAG fusion protein was driven by the signal sequence of VEGF-D. pEFBOSVEGFDfullFLAG was designed to drive expression in mammalian cells of full-length VEGF-D which was C-terminally tagged with the FLAG™ octapeptide. This protein is designated VEGFDfullFLAG, and is useful for the study of VEGF-D biosynthesis.

Analysis of the Post-Translational Processing of VEGF-D

Figure 12A:
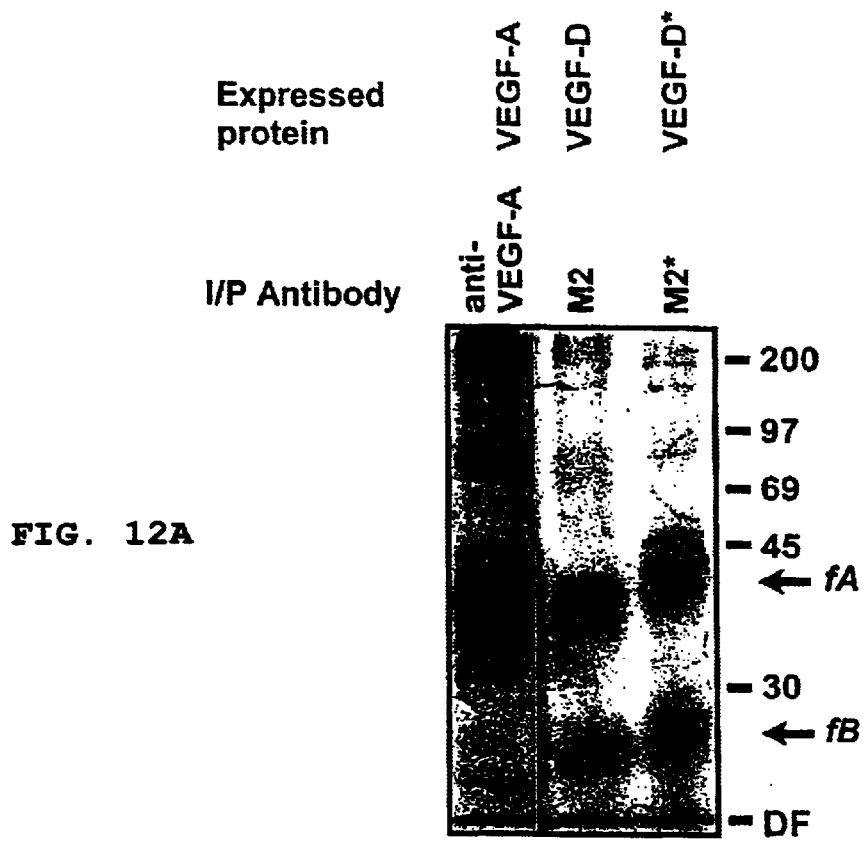
FIG. 12 shows the results of immunoprecipitation and Western blotting analysis of VEGF-D peptides (A) pEFBOSVEGFDfullFLAG and pcDNA-1VEGF-A were transfected into COS cells and biosynthetically labelled with $^{35}$S-cysteine/methionine for 4 hours. The supernatants from these cultures were immunoprecipitated with either M2 gel or an antiserum directed to VEGF-A coupled to protein A. Washed beads were eluted with an equal volume of 2×SDS-PAGE sample buffer and boiled. The samples were then resolved by 12% SDS-PAGE. Lanes marked with an asterix (*) indicate where samples were reduced with dithiothreitol and alkylated with iodoacetamide. Molecular weight markers are indicated. fA and fB indicate the 43 kD and 25 kD species immunoprecipitated by the M2 gel from the COS cells expressing pEFBOSVEd-FDfullFLAG.

To examine whether the VEGF-D polypeptide is processed to give a mature and fully active protein, pEFBOS-VEGFDfullFLAG was transiently transfected into COS cells (Aruffo and Seed, 1987). Expression in COS cells followed by biosynthetic labeling with $^{35}$S-methionine/cysteine and immunoprecipitation with M2 gel has demonstrated species of approximately 43 kD (fA) and 25 kD(fB) (FIG. 12A). These bands are consistent with the notion that VEGF-D is cleaved to give a C-terminal fragment (FLAG™ tagged) and an internal peptide (corresponding approximately to the VEGFDΔNΔC protein). Reduction of the immunoprecipitates (M2*) gives some reduction of the fA band, indicating the potential for disulphide linkage between the two fragments.

Expression and Purification of Internal VEGF-D Polypeptide

Plasmid pEFBOSVEGFDΔNΔC was used to transiently transfect COS cells by the DEAE-Dextran method as described previously (Aruffo and Seed, 1987). The resulting conditioned cell culture medium (approximately 150 ml), collected after 7 days of incubation, was subjected to affinity chromatography using a resin to which the M2 monoclonal antibody had been coupled. In brief, the medium was run batch-wise over a 1 ml M2 antibody column for approximately 4 hours at 4_C. The column was then washed extensively with 10 mM Tris-HCl, pH 8.0, 150 mM NaCl before elution with free FLAG™ peptide at 25 g/ml in the same buffer. The resulting material was used for the bioassays described below.

Figure 12B:
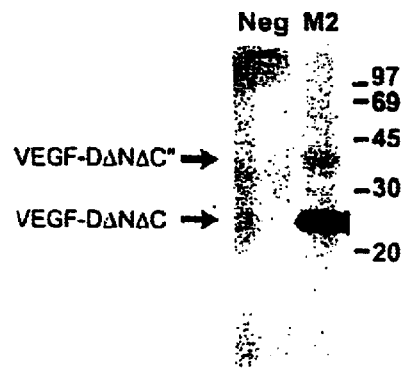

In order to detect the purified VEGFDΔNΔC, fractions eluted from the M2 affinity column were subjected to Western blot analysis. Aliquots of the column fractions were combined with 2xSDS-PAGE sample buffer, boiled and loaded onto a 15% SDS polyacrylamide gel. The resolved fractions were transferred to nitrocellulose membrane and non-specific binding sites blocked by incubation in Tris/NaCl/Tween 20 (TST) and 10% skim milk powder (BLOTTO). Membranes were then incubated with monoclonal antibody M2 or control antibody at 3 µg/ml for 2 h at room temperature, followed by extensive washing in TST. Membranes were then incubated with a secondary goat anti-mouse HRP-conjugated antiserum for 1 h at room temperature, followed by washing in TST buffer. Detection of the protein species was achieved using a chemiluminescent reagent (ECL, Amersham) (FIG. 12B).

Under non-reducing conditions a species of molecular weight approximately 23 kD (VEGFDΔNΔC) was detected by the M2 antibody. This is consistent with the predicted molecular weight for this internal fragment (12,800) plus N-linked glycosylation; VEGFDΔNΔC contains two potential N-linked glycosylation sites. A species of approximately 40 kD was also detected, and may represent a non-covalent dimer of the 23 kD protein (VEGFDΔNΔC).

Bioassays

The bioassay for the capacity of polypeptides to bind to VEGF receptor-2 is described in detail in Example 7. Aliquots of fractions eluted from the M2 affinity column, containing the VEGFDΔNΔC protein, were diluted in medium and tested in the VEGFR2 bioassay as previously described. Fraction #3 from the affinity column, which was shown to contain the purified VEGFDΔNΔC protein (FIG. 12B), demonstrated a clear ability to induce proliferation of the bioassay cell line to a dilution of 1/100 of the purified fraction (FIG. 13). In comparison, the void volume of the affinity column (fraction #1) showed no activity, whereas the original VEGFDΔNΔC conditioned medium gave only weak activity.

The vascular permeability assay (Miles and Miles, 1952) is described in brief in example 8. Aliquots of purified VEGFDΔNΔC, and samples of the void volume from the M2 affinity column (negative control) were combined with medium and injected intradermally into the skin of guinea pigs. The regions of skin at the sites of injections were excised, and extravasated dye was eluted. The absorbance of the extravasated dye at 620 nm arising from injection of purified VEGFDΔNΔC was 0.131±0.009. In comparison, the value for absorbance arising from injection of a sample of the void volume was 0.092±0.020. Therefore VEGFDΔNΔC induced vascular permeability, but the effect was only marginal.

Due to its ability to bind to VEGFR2 and its lower induction of vascular permeability compared to full length VEGF-D, VEGF-DΔNΔC may be said to relatively decrease the induction of vascular permeability by VEGF-D through competitive inhibition. In this sense, the VEGF-DΔNΔC fragment may be thought of as an antagonist for VEGF-D as regards the induction of vascular permeability.

Summary

Two factors have led us to explore internal fragments of VEGF-D for enhanced activity. Firstly, it is the central region of VEGF-D which exhibits amino acid homology with all other members of the VEGF family. Secondly, proteolytic processing which gives rise to internal bioactive polypeptides occurs for other growth factors such as PDGF-BB. In addition, the activity seen with the full length VEGF-D protein in COS cells was lower than for the corresponding conditioned medium from VEGF-A transfected COS cells.

It was predicted that the mature VEGF-D sequence would be derived from a fragment contained within residues 92–205, with cleavage at FAA^TFY (residues 60-65 of SEQ ID NO: 3) and IIRR^SIQI (residues 173-180 of SEQ ID NO: 3). Immunoprecipitation analysis of VEGF-DfullFLAG expressed in COS cells produced species consistent with the internal proteolytic cleavage of the VEGF-D polypeptide at these sites. Therefore a truncated form of VEGF-D, with the N- and C-terminal regions removed (VEGFDΔNΔC), was produced and expressed in COS cells. This protein was identified and purified using the M2 antibody. The VEGFDΔNΔC protein was also detected by the A2 antibody, which recognizes a peptide within the 92–205 fragment of VEGF-D (not shown). VEGFDΔNΔC was evaluated by the VEGFR2 bioassay and the Miles vascular permeability assay, and shown to bind to and activate the VEGFR2 receptor in a bioassay designed to detect cross-linking of the VEGFR2 extracellular domain. Induction of vascular permeability by this polypeptide in a Miles assay was at best marginal, in contrast to the effect of VEGF-A.

EXAMPLE 10

VEGF-D Binds to and Activates VEGFR-3

The human VEGF-D cDNA was cloned into baculovirus shuttle vectors for the production of recombinant VEGF-D. In addition to baculoviral shuttle vectors, which contained the unmodified VEGF-D cDNA (referred to as "full length VEGF-D") two baculoviral shuttle vectors were assembled, in which the VEGF-D cDNA was modified in the following ways.

In one construct (referred to as "full length VEGF-D-$H_6$") a C-terminal histidine tag was added. In the other construct the putative N- and C-terminal propeptides were removed, the melittin signal peptide was fused in-frame to the N-terminus, and a histidine tag was added to the C-terminus of the remaining VEGF homology domain (referred to as "Δ NAc-MELsp-VEGF-D-$H_6$").

For each of the three constructs baculoviral clones of two or three independent transfections were amplified The supernatant of High Five (HF) cells was harvested 48 h post infection with high titre virus stocks. The supernatant was adjusted to pH 7 with NaOH and diluted with one volume of D-MEM (0.2% FCS).

The samples were tested for their ability to stimulate tyrosine phosphorylation of VEGFR-3 (Flt-4 receptor) on NIH3T3 cells, as described by Joukov et al, 1996. The supernatant of uninfected cells and the supernatant of cells infected with the short splice variant of VEGF-C, which does not stimulate tyrosine phosphorylation of VEGFR-3, were used-as negative controls. VEGF-C modified in the same way as ΔNΔC-melSP-VEGF-D-$H_6$ was used as positive control. The results are shown in FIG. 14.

The appearance of new bands at 125 and 195 kD indicates phosphorylation, and hence activation, of the receptor.

EXAMPLE 11

VEGF-D Binds to and Activates VEGFR-2

Modified and unmodified human VEGF-D cDNA was cloned into baculovirus shuttle vectors for the production of recombinant VEGF-D as described in Example 10. For each of the three constructs full length VEGF-D, full length VEGF-D-$H_6$, and ΔNΔC-melSP-VEGF-D-$H_6$, baculoviral clones of two or three independent transfections were amplified. The supernatant of High Five (HF) cells was harvested 48 hours post infection with high titre virus stocks. The supernatant was adjusted to pH 7 with NaOH and diluted with one volume of D-MEM (0.2% FCS).

The supernatants conditioned with the histidine-tagged proteins were tested for their ability to stimulate tyrosine phosphorylation of the KDR receptor according to Joukov et al, 1996. KDR is the human homologue of flk1 (VEGFR-2).

The supernatant of uninfected cells and the supernatant of cells infected with the VEGF-C 156S mutant, which does not stimulate KDR, were used as negative controls.

VEGF$_{165}$ and VEGF-C modified in the same way as ΔNΔC-melSP-VEGF-D-H$_6$ were used as positive controls. The results are shown in FIG. 15.

The appearance of a new band at approximately 210 kD indicates phosphorylation, and hence activation, of the receptor.

EXAMPLE 12

Analysis of VEGF-D Gene Expression

In order to characterise the pattern of VEGF-D gene expression in the human and in mouse embryos, VEGF-D cDNAs were used as hybridization probes for Northern blot analysis of polyadenylated human RNA and for in situ hybridization analysis with mouse embryos.

Gene Expression in the Adult Human

A 1.1 kb fragment of the human VEGF-D cDNA shown in FIG. 4 (SEQ ID NO:4) spanning from the EcoRV site to the 3'-terminus (nucleotides 911 to 2029) was labelled with [α-$^{32}$P]dATP using the Megaprime DNA labelling system (Amersham) according to manufacturer's instructions. This probe was used to screen human multiple tissue northern blots (Clontech) by hybridization, also according to manufacturer's instructions. These blots contained polyadenylated RNA obtained from tissues of adult humans who were apparently free of disease. Autoradiography with the labelled blots revealed that VEGF-D mRNA was most abundant in heart, lung and skeletal muscle. VEGF-D mRNA was of intermediate abundance in spleen, ovary, small intestine and colon, and was of low abundance in kidney, pancreas, thymus, prostate and testis. No VEGF-D mRNA was detected in RNA from brain, placenta, liver or peripheral blood leukocytes. In most of the tissues where VEGF-D mRNA was detected the size of the transcript was 2.3 kb. The only exception was skeletal muscle, where two VEGF-D transcripts of 2.3 kb and 2.8 kb were detected. In skeletal muscle the 2.3 kb transcript was more abundant than the 2.8 kb transcript.

Gene Expression in Mouse Embryos

In order to generate an antisense RNA probe for mouse VEGF-D mRNA, the mouse VEGF-D2 cDNA shown in FIG. 7 (SEQ ID NO:7) was inserted into the transcription vector pBluescriptIIKS+ (Stratagene). The resulting plasmid was digested to completion with the restriction endonuclease FokI and then used as template for an in vitro transcription reaction with T3 RNA polymerase. This transcription reaction gave rise to an antisense RNA probe for VEGF-D mRNA which was complementary in sequence to the region of the VEGF-D2 cDNA (FIG. 7) from the 3'-terminus to the FokI cleavage site closest to the 3'-terminus (nucleotides 1135 to 700). This antisense RNA probe was hybridized at high stringency with paraffin-embedded tissue sections generated from mouse embryos at post-coital day 15.5. Hybridization and washing were essentially as described previously (Achen et al., 1995). After washing and drying, slides were exposed to autoradiography film for six days.

Development of the autoradiography film revealed that VEGF-D mRNA is localised in the developing lung of post-coital day 15.5 embryos. The signal for VEGF-D mRNA in the lung was strong and highly specific. Control hybridizations with sense probe gave no detectable background in lung or any other tissue.

Summary

The VEGF-D gene is broadly expressed in the adult human, but is certainly not ubiquitously expressed. Strongest expression was detected in heart, lung and skeletal muscle. In mouse embryos at post-coital day 15.5, strong and specific expression of the VEGF-D gene was detected in the lung. These data suggest that VEGF-D may play a role in lung development, and that expression of the VEGF-D gene in lung persists in the adult, at least in humans. Expression of the gene in other tissues in the adult human suggests that VEGF-D may fulfill other functions in other adult tissues.

EXAMPLE 13

VEGF-D is Mitogenic for Endothelial Cells

Some members of the VEGF family of proteins, namely VEGF-A (Leung et al, 1989) and VEGF-B (Olofsson et al, 1996), are mitogenic for endothelial cells. In order to test the mitogenic capacity of VEGFDΔNΔC for endothelial cells, this protein was expressed and purified by affinity chromatography as described in Example 9. Fraction #3, eluted from the M2 affinity column, which contained VEGFDΔNΔC, was diluted 1 in 10 in cell culture medium containing 5% serum and applied to bovine aortic endothelial cells (BAEs) which had been propagated in medium containing 10% serum. The BAEs had been seeded in 24-well dishes at a density of 10,000 cells per well the day before addition of VEGFDΔNΔC, and 3 days after addition of this polypeptide the cells were dissociated with trypsin and counted. Purified VEGF-A was included in the experiment as positive control. Results are shown in FIG. 16. The addition of fraction #3 to the cell culture medium led to a 2.4-fold increase in the number of BAEs after 3 days of incubation, a result which was comparable to that obtained with VEGF-A. Clearly VEGFDΔNΔC is mitogenic for endothelial cells.

EXAMPLE 14

Localization of the VEGF-D Gene on Human Chromosomes

In order to generate hybridization probes for localization of the VEGF-D gene on human chromosomes, a human genomic DNA clone for VEGF-D was isolated from a human genomic DNA library (Clontech). The genomic library was screened by hybridization with the human VEGF-D cDNA shown in FIG. 4, using standard methods (Sambrook et al., 1989). One of the clones thus isolated was shown to contain part of the VEGF-D gene by hybridization to numerous oligonucleotides which were derived in sequence from the human VEGF-D cDNA. A region of the genomic clone, approximately 13 kb in size, was purified from agarose gel, labelled by nick-translation with biotin-14-dATP and hybridized in situ at a final concentration of 20 ng/μl to metaphases from two normal human males. The fluorescence in situ hybridization (FISH) method was modified from that previously described (Callen et al, 1990) in that chromosomes were stained before analysis with propidium iodide (as counterstain) and DAPI (for chromosome identification). Images of metaphase preparations were captured by a cooled CCD camera, using the CytoVision Ultra image collection and enhancement system (Applied Imaging Int. Ltd.). FISH signals and the DAPI banding pattern were merged for analysis.

Fifteen metaphases from the first normal male were examined for fluorescent signal. Ten of the metaphases showed signal on one chromatid (3 cells) or both chromatids (7 cells) of the X chromosome in band p22.1. There was a total of 9 non-specific background dots observed in these 15 metaphases. A similar result was obtained from hybridization of the probe to 15 metaphases from the second normal male, where signal was observed at Xp22.1 on one chromatid in 7 cells and on both chromatids in 4 cells. In conclusion, the human VEGF-D gene is located on the X chromosome in band p22.1.

EXAMPLE 15

Localization of the Murine VEGF-D Gene on Mouse Chromosomes

The mouse chromosomal location of the VEGF-D gene was determined by interspecific backcross analysis using progeny generated by mating (C57BL/6J×Mus spretus)F1 females and CB7BL/67 males as described previously (Copeland and Jenkins, 1991). This interspecific backcross mapping panel has been typed for over 2400 loci that are well distributed among all the autosomes as well as the X chromosome (Copeland and Jenkins, 1991). C57BL/6J and M. spretus DNAs were digested with several enzymes and analyzed by Southern blot hybridization for informative restriction fragment length polymorphisms (RFLPs) using a 1.3 kb mouse VEGF-D cDNA probe essentially as described (Jenkins et al. 1982). Fragments of 7.1, 6.3, 4.7, 2.5 and 2.2 kb were detected in TaqI-digested C57BL/6J DNA and major fragments of 7.1, 3.7, 2.7 and 2.2 kb were detected in TaqI-digested M. spretus DNA. The presence or absence of the 3.7 and 2.7 TaqI M. spretus-specific fragments, which cosegregated, was followed in backcross mice. The mapping results indicated that the VEGF-D gene is located in the distal region of the mouse X chromosome linked to Bik, DxPasI and Ptmb4. Although 89 mice were analyzed for every marker, up to 133 mice were typed for some pairs of markers. Each locus was analyzed in pairwise combinations for recombination frequencies using the additional data. The ratios of the total number of mice exhibiting recombinant chromosomes to the total number of mice analyzed for each pair of loci and the most likely gene order are: centromere–Btk–14/121–DxPasI–3/99–VEGF-D–5/133–Ptmb4. The recombination frequencies [expressed as genetic distances in centiMorgans (cM)±the standard error], calculated using Map Manager (version 2.6.5), are–Btk–11.6+/–2.9–DxPasI–3.0+/–1.7–VEGF-D–3.8+/–1.7–Ptmb4. A description of the probes and RFLPs for the loci linked to the VEGF-D gene, including Btk, DxPasI and Ptmb4, has been reported previously (Hacfliger et al., 1992; Holloway et al., 1997).

We have compared our interspecific map of the X chromosome with a composite mouse linkage map that reports the map location of many uncloned mutations (provided from Mouse Genome Database, a computerized database maintained at The Jackson Library, Bar Harbor, Me.). The VEGF-D gene mapped in a region of the composite map that lacks mouse mutations with a phenotype that might be expected for an alteration in the locus for an endothelial cell mitogen. The distal region of the mouse X-chromosome shares a region of homology with the short arm of the human X chromosomes (Mouse Genome Database). The placement of the VEGF-D gene in this interval in mouse suggests that the human homolog will map to Xp22. This is consistent with our FISH analysis which has localized the human gene to Xp22.1.

Numerous disease states are caused by mutations in unknown genes which have been mapped to Xp22.1 and the positions immediately surrounding this region in the human. These disease states include Kallmann syndrome, ocular albinism (Nettleship-Falls type), ocular albinism and sensorineural deafness, Partington syndrome, spondyloepiphyseal dysplasia (late), retinitis pigmentosa 15, gonadal dysgenesis (XY female type), Nance-Horan cataract-dental syndrome, retinoschisis, Charcot-Marie-Tooth disease, F-cell production, hypomagnesemia, keratosis follicularis spinulosa decalvans, Coffin-Lowry syndrome, corneal dermoids, hypophosphatemia, agammaglobulinemia, Aicardi symdrome, hereditary hypophosphatemia II, mental retardation (non-dysmorphic), Opitz G syndrome, pigment disorder (reticulate), dosage-sensitive sex reversal, adrenal hypoplasia, retinitis pigmentosa-6, deafness 4 (congenital sensorineural) and Wilson-Turner syndrome. The positions of the genes involved in these disease states are documented in the OMIM gene map which is edited by Dr. Victor McKusick and colleagues at Johns Hopkins University (USA).

BIOASSAYS TO DETERMINE THE FUNCTION OF VEGF-D

Other assays are conducted to evaluate whether VEGF-D has similar activities to VEGF in relation to endothelial cell function, angiogenesis and wound healing. Further assays may also be performed, depending on the results of receptor binding distribution studies.

Assays of Endothelial Cell Function a) Endothelial Cell Proliferation

Endothelial cell growth assays are performed by methods well known in the art, eg. those of Ferrara & Henzel (1989), Gospodarowicz et al (1989), and/or Claffey et al, Biochim. Biophys. Acta, 1995 1246 1–9.

b) Cell Adhesion Assay

The effect of VEGF-D on adhesion of polmorphonuclear granulocytes to endothelial cells is tested.

c) Chemotaxis

The standard Boyden chamber chemotaxis assay is used to test the effect of VEGF-D on chemotaxis.

d) Plasminogen Activator Assay

Endothelial cells are tested for the effect of VEGF-D on plasminogen activator and plasminogen activator inhibitor production, using the method of Pepper et al (1991).

e) Endothelial Cell Migration Assay

The ability of VEGF-D to stimulate endothelial cells to migrate and form tubes is assayed as described in Montesano et al (1986). Alternatively, the three-dimensional collagen gel assay described by Joukov et al (1996) or a gelatinized membrane in a modified Boyden chamber (Glaser et al, 1980) may be used.

II Angiogenesis Assay

The ability of VEGF-D to induce an angiogenic response in chick chorioallantoic membrane is tested as described in Leung et al (1989). Alternatively the rat cornea assay of Rastinejad et al (1989) may be used; this is an accepted method for assay of in vivo angiogenesis, and the results are readily transferrable to other in vivo systems.

III Wound Healing

The ability of VEGF-D to stimulate wound healing is tested in the most clinically relevant model available, as described in Schilling et al (1959) and utilised by Hunt et al (1967).

IV The Haemopoietic System

A variety of in vitro and in vivo assays using specific cell populations of the haemopoietic system are known in the art, and are outlined below. In particular a variety of in vitro murine stem cell assays using fluorescence-activated cell sorter purified cells are particularly convenient:

a) Repopulating Stem Cells

These are cells capable of repopulating the bone marrow of lethally irradiated mice, and have the Lin⁻, $Rh^{h1}$, Ly-6A/E⁺, c-kit⁺ phenotype. VEGF-D is tested on these cells either alone, or by co-incubation with other factors, followed by measurement of cellular proliferation by $^3$H-thymidine incorporation.

b) Late Stage Stem Cells

These are cells that have comparatively little bone marrow repopulating ability, but can generate D13 CFU-S. These cells have the Lin⁻, $Rh^{h1}$, Ly-6A/E⁺, c-kit⁺ phenotype. VEGF-D is incubated with these cells for a period of time, injected into lethally irradiated recipients, and the number of D13 spleen colonies enumerated.

c) Progenitor-Enriched Cells

These are cells that respond in vitro to single growth factors and have the Lin⁻, $Rh^{h1}$, Ly-6A/E⁺, c-kit⁺ phenotype. This assay will show if VEGF-D can act directly on haemopoietic progenitor cells. VEGF-D is incubated with these cells in agar cultures, and the number of colonies present after 7–14 days is counted.

V Atherosclerosis

Smooth muscle cells play a crucial role in the development or initiation of atherosclerosis, requiring a change of their phenotype from a contractile to a synthetic state. Macrophages, endothelial cells, T lymphocytes and platelets all play a role in the development of atherosclerotic plaques by influencing the growth and phenotypic modulations of smooth muscle cell. An in vitro assay using a modified Rose chamber in which different cell types are seeded on to opposite coverslips measures the proliferative rate and phenotypic modulations of smooth muscle cells in a multicellular environment, and is used to assess the effect of VEGF-D on smooth muscle cells.

VI Metastasis

The ability of VEGF-D to inhibit metastasis is assayed using the Lewis lung carcinoma model, for example using the method of Cao et al (1995).

VII VEGF-D in Other Cell Types

The effects of VEGF-D on proliferation, differentiation and function of other cell types, such as liver cells, cardiac muscle and other cells, endocrine cells and osteoblasts can readily be assayed by methods known in the art, such as $^3$H-thymidine uptake by in vitro cultures. Expression of VEGF-D in these and other tissues can be measured by techniques such as Northern blotting and hybridization or by in situ hybridization.

VIII Construction of VEGF-D Variants and Analogues

VEGF-D is a member of the PDGF family of growth factors which exhibits a high degree of homology to the other members of the PDGF family. VEGF-D contains eight conserved cysteine residues which are characteristic of this family of growth factors. These conserved cysteine residues form intra-chain disulfide bonds which produce the cysteine knot structure, and inter-chain disulfide bonds that form the protein dimers which are characteristic of members of the PDGF family of growth factors. VEGF-D will interact with protein tyrosine kinase growth factor receptors.

In contrast to proteins where little or nothing is known about the protein structure and active sites needed for receptor binding and consequent activity, the design of active mutants of VEGF-D is greatly facilitated by the fact that a great deal is known about the active sites and important amino acids of the members of the PDGF family of growth factors.

Published articles elucidating the structure/activity relationships of members of the PDGF family of growth factors include for PDGF: Oestman et al, J. Biol. Chem., 1991 266 10073–10077; Andersson et al, J. Biol. Chem., 1992 267 11260–1266; Oefner et al, EMBO J., 1992 11 3921–3926; Flemming et al, Molecular and Cell Biol., 1993 13 4066–4076 and Andersson et al, Growth Factors, 1995 12 159–164; and for VEGF: Kim et al, Growth Factors, 1992 7 53–64; Pötgens et al, J. Biol. Chem., 1994 269 32879–32885 and Claffey et al, Biochem. Biophys. Acta, 1995 1246 1–9. From these publications it is apparent that because of the eight conserved cysteine residues, the members of the PDGF family of growth factors exhibit a characteristic knotted folding structure and dimerization, which result in formation of three exposed loop regions at each end of the dimerized molecule, at which the active receptor binding sites can be expected to be located.

Based on this information, a person'skilled in the biotechnology arts can design VEGF-D mutants with a very high probability of retaining VEGF-D activity by conserving the eight cysteine residues responsible for the knotted folding arrangement and for dimerization, and also by conserving, or making only conservative amino acid substitutions in the likely receptor sequences in the loop 1, loop 2 and loop 3 region of the protein structure.

The formation of desired mutations at specifically targeted sites in a protein structure is considered to be a standard technique in the arsenal of the protein chemist (Kunkel et al, Methods in Enzymol., 1987 154 367–382). Examples of such site-directed mutagenesis with VEGF can be found in Pötgens et al, J. Biol. Chem., 1994 269 32879–32885 and Claffey et al, Biochim. Biophys. Acta, 1995 1246 1–9. Indeed, site-directed mutagenesis is so common that kits are commercially available to facilitate such procedures (eg. Promega 1994–1995 Catalog., Pages 142–145).

The endothelial cell proliferating activity of VEGF-D mutants can be readily confirmed by well established screening procedures. For example, a procedure analogous to the endothelial cell mitotic assay described by Claffey et al, (Biochim. Biophys. Acta., 1995 1246 1–9) can be used. Similarly the effects of VEGF-D on proliferation of other cell types, on cellular differentiation and on human metastasis can be tested using methods which are well known in the art.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Achen, M. G., Clauss, M., Schnürch, H. and Risau, W. Differentiation, 1995 59 15–24

Andersson, M., Östman, A., Bäckström, G., Hellman, U., George-Nascimento, C., Westermark, B. and Heldin, C-H. J. Biol. Chem., 1992 267 11260–1266

Anderson, M, Östman, A., Kreysing, J., Bäckström, G. van de Poll, M. and Heldin, C-H. Growth Factors, 1995 12 159–164

Aruffo, A. and Seed, B. Proc. Natl. Acad. Sci. USA., 1987 84 8573–8577

Callen, D. F., Baker, E., Eyre, H. J., Chermos, J. E., Bell, J. A. and Sutherland, G. R. Ann. Genet., 1990 33 219–221

Claffey, K. P., Senger, D. R., Spiegelman, B. M. Biochem. Biophys. Acta, 1995 1246 1–9

Cao, Y. Chen, C., Weatherbee, J. A., Tsang, M. and Folkman, J. J. Exp. Med., 1995 182 2069–2077

Copeland, N. G. and Jenkins N. A. Trends Genet., 1991 7 113–118

Ferrara, N. & Henzel, W. J. Biochem. Biophys. Res. Commun., 1989 161 851–858

Flemming, S. V., Andersson, M., Westermark, B., Heldin, C-H. and Östman, A. Molecular and Cell Biol., 1993 13 4066–4076

Glaser, B. M. and D'Amore, P. A. Nature, 1980 288 483–484

Gospodarowicz, D., Abraham, J. A., Schilling, J. Proc. Natl. Acad. Sci. USA, 1989 86 7311–7315

Haefliger, J-A., Bruzzone, R., Jenkins, N. A., Gilbert, D. J., Copeland, N. G. and Paul D. L. 1992 J. Biol. Chem., 1992 267 2057–2064

Holloway. A. J., Della N. G., Fletcher, C. F., Largaespada, D. A., Copeland, N. G., Jenkins, N. A. and Bowtell D. D. L. Genomics, 1997 41 160–168

Hunt et al Am. J. Surgery, 1967 114 302–307

Jenkins, N. A., Copeland, N. G., Taylor, B. A. and Lee, B. K. J. Virol. 1982 43 26–36

Joukov, V., Pajusola, K., Kaipainen, A., Chilov, D., Lahtinen, I., Kukk, E., Saksela, O., Kalkkinen, N. and Alitalo, K. EMBO Journal, 1996 15 290–298

Kim, K. J., Li, B., Houck, K. Winner, J. and Ferrara, N. Growth Factors, 1992 7 53–64

Kunkel, T. A., Roberts, J. D. and Zakour, R. A. Methods in Enzymol., 1987 154 367–382

Leung, D. W., Cachianes, G., Kuang, W-J., Goeddel, D. V. and Ferrara, N. Science, 1989 246 1306–1309

Miles, A. A. and Miles, E. M. J. Physiol. (London), 1952 118 228–257

Montesano, R., Vassalli, J. D., Baird, A., Guillemin, R. and Orci, L. Proc. Natl. Acad. Sci. USA, 1986 83 7297–7301

Oefner, C., D'Arcy, A., Winkler, F. K., Eggimann, B. and Hosang, M. EMBO Journal, 1992 11 3921–3926

Oelrichs, R. B., Reid, H. H., Bernard, O., Ziemiecki, A. and Wilks, A. F. Oncogene, 1993 8 11–18

Oestman, A., Andersson, M., Hellman, U. and Heldin, C-H. J. Biol. Chem., 1991 266 10073–10077

Olofsson, B., Pajusola, K., Kaipainen, A., von Euler, G., Joukov, V., Saksela, O., Orpana, A., Pettersson, R. F., Alitalo, K and Eriksson, U. Proc. Natl. Acad. Sci. USA., 1996 93 2576–2581

Pepper, M. S., Ferrara, N. Orci, L. and Montesano. R. Biochem. Biophys. Res. Commun., 1991 181 902–906

Pötgens, A. J., Lubsen, N. H., van Altena, M. C., Vermeulen, R., Bakker, A., Schoenmakers, J. G. G., Ruiter, D. J. and de Waal, R. M. W. J. Biol. Chem., 1994 269 32879–32885

Rastinejad, F., Plverini, P. J. and Bouck, N. P. Cell, 1989 56 345–355

Sambrook, J., Fritsch, E. F. and Maniatis, T. Molecular Cloning. A Laboratory Manual. Second edition. Cold Spring Harbor Laboratory Press, Cold Spring Harbor, N.Y.

Schilling et al Surgery, 1959 46 702–710

Strawn, L. M., McMahon, G., App, H., Schreck, R., Kuchler, W. R., Longhi, M. P., Hui, T. H., Tang, C., Levitzki, A., Gazit, A., Chen, I., Keri, G., Orfi, L., Risau, W., Flamme, I., Ullrich, A., Hirth, K. P. and Shawver, L. K. Cancer Res., 1996 56 3540–3545

---

What is claimed is:

1. An isolated nucleic acid molecule comprising a nucleic acid sequence which encodes a polypeptide comprising a sequence of amino acids corresponding to the amino acid sequence set out in SEQ ID NO:3, SEQ ID NO:8 or SEQ ID NO:9, said polypeptide having the ability to stimulate vascular permeability or proliferation of endothelial cells, or a fragment thereof which has the ability to stimulate at least one biological activity selected from the group consisting of angiogenesis, vascular permeability, endothelial cell proliferation, differentiation, migration or survival.

2. A nucleic acid molecule according to claim 1, wherein said endothelial cells are selected from the group consisting of vascular endothelial cells and lymphatic endothelial cells.

3. A nucleic acid molecule according to claim 1, which is a cDNA.

4. A nucleic acid molecule according to claim 1, which encodes a polypeptide which has the ability to stimulate vascular permeability or proliferation of endothelial cells.

5. A nucleic acid molecule according to claim 1, which encodes a polypeptide comprising amino acid residues 64 through 172 of SEQ ID NO:3.

6. A nucleic acid molecule according to claim 5, wherein said polypeptide further comprises an affinity tag peptide sequence.

7. A nucleic acid molecule according to claim 1, wherein said nucleic acid molecule is a human DNA molecule.

8. A vector comprising a nucleic acid according to claim 1.

9. A host cell transformed or transfected with a vector according to claim 8.

10. A method of making a polypeptide, said method comprising the steps of:

culturing a host cell transformed or transfected with a vector comprising a nucleic acid sequence according to claim 1, operably associated with a promoter sequence such that a polypeptide encoded by the nucleic acid sequence is expressed; and isolating said polypeptide from said host cell or from a growth medium in which said host cell is cultured.

11. A method of isolation of a polypeptide, said method comprising the step of exposing a cell which expresses a polypeptide encoded by a nucleic acid molecule according to claim 1, to heparin to facilitate release of the polypeptide from the cell, and recovering the thus-released polypeptide.

12. A method of making a vector comprising a nucleic acid molecule according to claim 1, said method comprising inserting said nucleic acid molecule into a vector in a position in which said nucleic acid molecule is operatively connected with at least one promoter.

13. A nucleic acid molecule which comprises the nucleic acid sequence of SEQ ID NO: 4.

14. A nucleic acid molecule which comprises a nucleic acid sequence selected from the group consisting of SEQ ID NO:1, SEQ ID NO:4, SEQ ID NO:6, SEQ ID NO:7, and sequences complimentary to SEQ ID NO:1, SEQ ID NO:4, SEQ ID NO:6, or SEQ ID NO:7.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 2846 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (vi) ORIGINAL SOURCE:
      (F) TISSUE TYPE: Human Breast (xi) SEQUENCE DESCRIPTION: SEQ ID NO:1:

```
GGAATTCAGT GAAGTAAGAA AGACAAAGTG TTCATTGGAG ATTTTTAGTA AGGGGCCAAC      60

AGAGCTGCTA AAGTCATGCT TCACTTAACG ATGGGGATAT GTTCGGAGAA ATGCATTGTT     120

AGGTGATTTT GTCGTTGTGC AAGCATCTTA GAGTACACTT AGACAAACCT AGCTGGTATA     180

ACCTAGGTGT GTAGTAGGAT ATATGGTATA GCCTATTGTT CCTAGGCTAC AAACCCATAC     240

AGCATGTTCC TGTACTGAAT ACTGAGGCAA CTGCAACACC GTGGTGAGTA TTTGTGTATC     300
```

```
TAAACATACC TAAACATAGA AAAGATACAG TAAAAATATG GCATTATAGT CTTATGGGAC    360

TACTGTCATA CATACAGTCC ATATATTGTT GACTGTGTAA TGTTGACCTG AATGTCATTA    420

TGTGGCAGGC ACATGACTGT GTCGCTAACC TTTGCACAAG ATTACTGTAG GATTACATGA    480

GATAGTTGTA AATAATTGGT GGGGTACTGG GCACCTAGTA GGTATGCATA CATGTTCACC    540

ATCATTATGG TTGTTTTAAA TCACCTAACC CAGGCCCTGC ACATAGTAAG ACATCAACAA    600

ATTGTAGCTG CTACTATTTT GCGCATCTAA TCTTAATATC ATTTATTTTG TAGTCCTTGG    660

ATGTTCCCTC CTTTATGACT TCTTTTTTTT TTGTTGTCCT TCCTTTAGCC CTCCATCCTC    720

TACAGCTCAG CATCAGAACA CTCTCTTTTT AGACTCCGAT ATGGGGTCCT CCAAGAAAGT    780

TACTCTCTCA GTGCTCAGCC GGGAGCAGTC GGAAGGGGTT GGAGCGAGGG TCCGGAGAAG    840

CATTGGCAGA CCCGAGTTAA AAAATCTGGA TCCGTTTTTA CTGTTTGATG AATTTAAAGG    900

AGGTAGACCA GGAGGATTTC CTGATCATCC ACATCGAGGT TTTGAAACAG TATCCTACCT    960

CCTGGAAGGG GGCAGCATGG CCCATGAAGA CTTCTGTGGA CACACTGGTA AAATGAACCC   1020

AGGAGATTTG CAGTGGATGA CTGCGGGCCG GGGCATTCTG CACGCTGAGA TGCCTTGCTC   1080

AGAGGAGCCA GCCCATGGCC TACAACTGTG GGTTAATTTG AGGAGCTCAG AGAAGATGGT   1140

GGAGCCTCAG TACCAGGAAC TGAAAAGTGA AGAAATCCCT AAACCCAGTA AGGATGGTGT   1200

GACAGTTGCT GTCATTTCTG GAGAAGCCCT GGGAATAAAG TCCAAGGTTT ACACTCGCAC   1260

ACCAACCTTA TATTTGGACT TCAAATTGGA CCCAGGAGCC AAACATTCCC AACCTATCCC   1320

TAAAGGGTGG ACAAGCTTCA TTTACACGAT ATCTGGAGAT GTGTATATTG CCCTCTCTAT   1380

ATCCCAGCAC AGGTATGCCC AGGGCAGGGT GCCTTTCAGC TTACAGAACA TTCAGTGAGG   1440

GAAGAGAATA TGAACACCAG TCATGACACA TCCTGTGCAC AGATGAAAGT CCAGGCACCA   1500

TTATGTGTTT TGATACCTCG CTAAGACGTT GGCAACCTCC ATACTGATAA AGGGATGGAG   1560

CTACAGTGGA CTCCAAGGGG AGCAGGAATC TGCCTATCTC CTGGGAGAAG GAAATGGAAG   1620

GAGGGCCCGA TGATGCACAA CAAAAAATAG AACCTCATCA CACAGCAGTG CTTGGAGAAG   1680

GTGACAGTGT CCAAGTGGAG AACAAGGATC CCAAGAGAAG CCACTTTGTC TTAATTGCTG   1740

GGGAGCCATT AAGAGAACCA GTTATCCAAC ATGCGATCAT CTCAGTCCAC ATTGGAACGA   1800

TCTGAACAGC AGATCAGGGC TGCTTCTAGT TTGGAGGAAC TACTTCGAAT TACTCACTCT   1860

GAGGACTGGA AGCTGTGGAG ATGCAGGCTG AGGCTCAAAA GTTTTACCAG TATGGACTCT   1920

CGCTCAGCAT CCCATCGGTC CACTAGGTTT GCGGCAACTT TCTATGACAT TGAAACACTA   1980

AAAGTTATAG ATGAAGAATG GCAAAGAACT CAGTGCAGCC CTAGAGAAAC GTGCGTGGAG   2040

GTGGCCAGTG AGCTGGGGAA GAGTACCAAC ACATTCTTCA AGCCCCCTTG TGTGAACGTG   2100

TTCCGATGTG GTGGCTGTTG CAATGAAGAG AGCCTTATCT GTATGAACAC CAGCACCTCG   2160

TACATTTCCA AACAGCTCTT TGAGATATCA GTGCCTTTGA CATCAGTACC TGAATTAGTG   2220

CCTGTTAAAG TTGCCAATCA TACAGGTTGT AAGTGCTTGC CAACAGCCCC CCGCCATCCA   2280

TACTCAATTA TCAGAAGATC CATCCAGATC CCTGAAGAAG ATCGCTGTTC CCATTCCAAG   2340

AAACTCTGTC CTATTGACAT GCTATGGGAT AGCAACAAAT GTAAATGTGT TTTGCAGGAG   2400

GAAAATCCAC TCGCTGGAAC AGAAGACCAC TCTCATCTCC AGGAACCAGC TCTCTGTGGG   2460

CCACACATGA TGTTTGACGA AGATCGTTGC GAGTGTGTCT GTAAAACACC ATGTCCCAAA   2520

GATCTAATCC AGCACCCCAA AAACTGCAGT TGCTTTGAGT GCAAAGAAAG TCTGGAGACC   2580

TGCTGCCAGA AGCACAAGCT ATTTCACCCA GACACCTGCA GCTGTGAGGA CAGATGCCCC   2640
```

```
TTTCATACCA GACCATGTGC AAGTGGCAAA ACAGCATGTG CAAAGCATTG CCGCTTTCCA    2700

AAGGAGAAAA GGGCTGCCCA GGGGCCCCAC AGCCGAAAGA ATCCTTGATT CAGCGTTCCA    2760

AGTTCCCCAT CCCTGTCATT TTTAACAGCA TGCTGCTTTG CCAAGTTGCT GTCACTGTTT    2820

TTTTCCCAGG TGTTAAAAAA AAAAAA                                         2846
```

(2) INFORMATION FOR SEQ ID NO:2:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:2:

```
Pro Xaa Cys Val Xaa Xaa Xaa Arg Cys Xaa Gly Cys Cys
1               5                   10
```

(2) INFORMATION FOR SEQ ID NO:3:

(i) SEQUENCE CHARACTERISTICS:
        (A) LENGTH: 325 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (F) TISSUE TYPE: Human Breast (xi) SEQUENCE DESCRIPTION: SEQ ID NO:3:

```
Met Arg Ser Ser Gln Ser Thr Leu Glu Arg Ser Glu Gln Gln Ile Arg
1               5                   10                  15

Ala Ala Ser Ser Leu Glu Glu Leu Leu Arg Ile Thr His Ser Glu Asp
                20                  25                  30

Trp Lys Leu Trp Arg Cys Arg Leu Arg Leu Lys Ser Phe Thr Ser Met
            35                  40                  45

Asp Ser Arg Ser Ala Ser His Arg Ser Thr Arg Phe Ala Ala Thr Phe
    50                  55                  60

Tyr Asp Ile Glu Thr Leu Lys Val Ile Asp Glu Glu Trp Gln Arg Thr
65                  70                  75                  80

Gln Cys Ser Pro Arg Glu Thr Cys Val Glu Val Ala Ser Glu Leu Gly
                85                  90                  95

Lys Ser Thr Asn Thr Phe Phe Lys Pro Pro Cys Val Asn Val Phe Arg
                100                 105                 110

Cys Gly Gly Cys Cys Asn Glu Glu Ser Leu Ile Cys Met Asn Thr Ser
            115                 120                 125

Thr Ser Tyr Ile Ser Lys Gln Leu Phe Glu Ile Ser Val Pro Leu Thr
    130                 135                 140

Ser Val Pro Glu Leu Val Pro Val Lys Val Ala Asn His Thr Gly Cys
145                 150                 155                 160

Lys Cys Leu Pro Thr Ala Pro Arg His Pro Tyr Ser Ile Ile Arg Arg
                165                 170                 175

Ser Ile Gln Ile Pro Glu Glu Asp Arg Cys Ser His Ser Lys Lys Leu
            180                 185                 190
```

```
Cys Pro Ile Asp Met Leu Trp Asp Ser Asn Lys Cys Lys Cys Val Leu
        195                 200                 205

Gln Glu Glu Asn Pro Leu Ala Gly Thr Glu Asp His Ser His Leu Gln
        210                 215                 220

Glu Pro Ala Leu Cys Gly Pro His Met Met Phe Asp Glu Asp Arg Cys
225                 230                 235                 240

Glu Cys Val Cys Lys Thr Pro Cys Pro Lys Asp Leu Ile Gln His Pro
                245                 250                 255

Lys Asn Cys Ser Cys Phe Glu Cys Lys Glu Ser Leu Glu Thr Cys Cys
            260                 265                 270

Gln Lys His Lys Leu Phe His Pro Asp Thr Cys Ser Cys Glu Asp Arg
        275                 280                 285

Cys Pro Phe His Thr Arg Pro Cys Ala Ser Gly Lys Thr Ala Cys Ala
290                 295                 300

Lys His Cys Arg Phe Pro Lys Glu Lys Arg Ala Ala Gln Gly Pro His
305                 310                 315                 320

Ser Arg Lys Asn Pro
            325

(2) INFORMATION FOR SEQ ID NO:4:

(i) SEQUENCE CHARACTERISTICS:
        (A) LENGTH: 2029 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (F) TISSUE TYPE: Human Lung (xi) SEQUENCE DESCRIPTION: SEQ ID NO:4:

GTTGGGTTCC AGCTTTCTGT AGCTGTAAGC ATTGGTGGCC ACACCACCTC CTTACAAAGC      60

AACTAGAACC TGCGGCATAC ATTGGAGAGA TTTTTTTAAT TTTCTGGACA TGAAGTAAAT     120

TTAGAGTGCT TTCTAATTTC AGGTAGAAGA CATGTCCACC TTCTGATTAT TTTTGGAGAA     180

CATTTTGATT TTTTTCATCT CTCTCTCCCC ACCCCTAAGA TTGTGCAAAA AAAGCGTACC     240

TTGCCTAATT GAAATAATTT CATTGGATTT TGATCAGAAC TGATTATTTG GTTTTCTGTG     300

TGAAGTTTTG AGGTTTCAAA CTTTCCTTCT GGAGAATGCC TTTTGAAACA ATTTTCTCTA     360

GCTGCCTGAT GTCAACTGCT TAGTAATCAG TGGATATTGA AATATTCAAA ATGTACAGAG     420

AGTGGGTAGT GGTGAATGTT TTCATGATGT TGTACGTCCA GCTGGTGCAG GGCTCCAGTA     480

ATGAACATGG ACCAGTGAAG CGATCATCTC AGTCCACATT GGAACGATCT GAACAGCAGA     540

TCAGGGCTGC TTCTAGTTTG GAGGAACTAC TTCGAATTAC TCACTCTGAG GACTGGAAGC     600

TGTGGAGATG CAGGCTGAGG CTCAAAAGTT TTACCAGTAT GGACTCTCGC TCAGCATCCC     660

ATCGGTCCAC TAGGTTTGCG GCAACTTTCT ATGACATTGA AACACTAAAA GTTATAGATG     720

AAGAATGGCA AAGAACTCAG TGCAGCCCTA GAGAAACGTG CGTGGAGGTG GCCAGTGAGC     780

TGGGGAAGAG TACCAACACA TTCTTCAAGC CCCCTTGTGT GAACGTGTTC CGATGTGGTG     840

GCTGTTGCAA TGAAGAGAGC CTTATCTGTA TGAACACCAG CACCTCGTAC ATTTCCAAAC     900

AGCTCTTTGA GATATCAGTG CCTTTGACAT CAGTACCTGA ATTAGTGCCT GTTAAAGTTG     960

CCAATCATAC AGGTTGTAAG TGCTTGCCAA CAGCCCCCCG CCATCCATAC TCAATTATCA    1020
```

```
GAAGATCCAT CCAGATCCCT GAAGAAGATC GCTGTTCCCA TTCCAAGAAA CTCTGTCCTA      1080

TTGACATGCT ATGGGATAGC AACAAATGTA AATGTGTTTT GCAGGAGGAA AATCCACTTG      1140

CTGGAACAGA AGACCACTCT CATCTCCAGG AACCAGCTCT CTGTGGGCCA CACATGATGT      1200

TTGACGAAGA TCGTTGCGAG TGTGTCTGTA AAACACCATG TCCCAAAGAT CTAATCCAGC      1260

ACCCCAAAAA CTGCAGTTGC TTTGAGTGCA AAGAAAGTCT GGAGACCTGC TGCCAGAAGC      1320

ACAAGCTATT TCACCCAGAC ACCTGCAGCT GTGAGGACAG ATGCCCCTTT CATACCAGAC      1380

CATGTGCAAG TGGCAAAACA GCATGTGCAA AGCATTGCCG CTTTCCAAAG GAGAAAAGGG      1440

CTGCCCAGGG GCCCCACAGC CGAAAGAATC CTTGATTCAG CGTTCCAAGT TCCCCATCCC      1500

TGTCATTTTT AACAGCATGC TGCTTTGCCA AGTTGCTGTC ACTGTTTTTT TCCCAGGTGT      1560

TAAAAAAAAA ATCCATTTTA CACAGCACCA CAGTGAATCC AGACCAACCT TCCATTCACA      1620

CCAGCTAAGG AGTCCCTGGT TCATTGATGG ATGTCTTCTA GCTGCAGATG CCTCTGCGCA      1680

CCAAGGAATG GAGAGGAGGG GACCCATGTA ATCCTTTTGT TTAGTTTTGT TTTTGTTTTT      1740

TGGTGAATGA GAAAGGTGTG CTGGTCATGG AATGGCAGGT GTCATATGAC TGATTACTCA      1800

GAGCAGATGA GGAAAACTGT AGTCTCTGAG TCCTTTGCTA ATCGCAACTC TTGTGAATTA      1860

TTCTGATTCT TTTTTATGCA GAATTTGATT CGTATGATCA GTACTGACTT TCTGATTACT      1920

GTCCAGCTTA TAGTCTTCCA GTTTAATGAA CTACCATCTG ATGTTTCATA TTTAAGTGTA      1980

TTTAAAGAAA ATAAACACCA TTATTCAAGC CAAAAAAAAA AAAAAAAA                   2029

(2) INFORMATION FOR SEQ ID NO:5:

(i) SEQUENCE CHARACTERISTICS:
        (A) LENGTH: 354 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
         (F) TISSUE TYPE: Human Lung (xi) SEQUENCE DESCRIPTION: SEQ ID NO:5:

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
                85                  90                  95

Glu Thr Leu Lys Val Ile Asp Glu Glu Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140
```

```
Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
            165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
            195                 200                 205

Ile Pro Glu Glu Asp Arg Cys Ser His Ser Lys Lys Leu Cys Pro Ile
    210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
            245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
            275                 280                 285

Ser Cys Phe Glu Cys Lys Glu Ser Leu Glu Thr Cys Cys Gln Lys His
            290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
            325                 330                 335

Arg Phe Pro Lys Glu Lys Arg Ala Ala Gln Gly Pro His Ser Arg Lys
            340                 345                 350

Asn Pro (2) INFORMATION FOR SEQ ID NO:6:

(i) SEQUENCE CHARACTERISTICS:
        (A) LENGTH: 1325 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (F) TISSUE TYPE: Mouse Lung (xi) SEQUENCE DESCRIPTION: SEQ ID NO:6:

GGAGAATGCC TTTTGCAACA CTTTTCAGTA GCTGCCTGGA ACAACTGCT TAGTCATCGG      60

TAGACATTTA AAATATTCAA AATGTATGGA GAATGGGGAA TGGGGAATAT CCTCATGATG   120

TTCCATGTGT ACTTGGTGCA GGGCTTCAGG AGCGAACATG GACCAGTGAA GGATTTTTCT   180

TTTGAGCGAT CATCCCGGTC CATGTTGGAA CGATCTGAAC AACAGATCCG AGCAGCTTCT   240

AGTTTGGAGG AGTTGCTGCA AATCGCGCAC TCTGAGGACT GGAAGCTGTG GCGATGCCGG   300

TTGAAGCTCA AAAGTCTTGC CAGTATGGAC TCACGCTCAG CATCCCATCG CTCCACCAGA   360

TTTGCGGCAA CTTTCTATGA CACTGAAACA CTAAAAGTTA TAGATGAAGA ATGGCAGAGG   420

ACCCAATGCA GCCCTAGAGA GACATGCGTA GAAGTCGCCA GTGAGCTGGG AAGACAACC   480

AACACATTCT TCAAGCCCCC CTGTGTAAAT GTCTTCCGGT GTGGAGGCTG CTGCAACGAA   540

GAGGGTGTGA TGTGTATGAA CACAAGCACC TCCTACATCT CCAAACAGCT CTTTGAGATA   600
```

```
TCAGTGCCTC TGACATCAGT GCCCGAGTTA GTGCCTGTTA AAATTGCCAA CCATACGGGT      660

TGTAAGTGCT TGCCCACGGG CCCCCGCCAT CCTTACTCAA TTATCAGAAG ATCCATTCAG      720

ACCCCAGAAG AAGATGAATG TCCTCATTCC AAGAAACTCT GTCCTATTGA CATGCTGTGG      780

GATAACACCA AATGTAAATG TGTTTTGCAA GACGAGACTC CACTGCCTGG ACAGAAGAC       840

CACTCTTACC TCCAGGAACC CACTCTCTGT GGACCGCACA TGACGTTTGA TGAAGATCGC      900

TGTGAGTGCG TCTGTAAAGC ACCATGTCCG GGAGATCTCA TTCAGCACCC GGAAAACTGC      960

AGTTGCTTTG AGTGCAAAGA AAGTCTGGAG AGCTGCTGCC AAAAGCACAA GATTTTTCAC     1020

CCAGACACCT GCAGCTGTGA GGACAGATGT CCTTTTCACA CCAGAACATG TGCAAGTAGA     1080

AAGCCAGCCT GTGGAAAGCA CTGGCGCTTT CCAAAGGAGA CAAGGGCCCA GGACTCTAC      1140

AGCCAGGAGA ACCCTTGATT CAACTTCCTT TCAAGTCCCC CCATCTCTGT CATTTTAAAC     1200

AGCTCACTGC TTTGTCAAGT TGCTGTCACT GTTGCCCACT ACCCCTTGAA CATGTGCAAA     1260

CACAGACACA CACACACACA CACACACAGA GCAACTAGAA TTATGTTTTC TAGGTGCTGC     1320

CTAAG                                                                1325

(2) INFORMATION FOR SEQ ID NO:7:

(i) SEQUENCE CHARACTERISTICS:
        (A) LENGTH: 1135 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
         (F) TISSUE TYPE: Mouse Lung (xi) SEQUENCE DESCRIPTION: SEQ ID NO:7:

AAACTTTGCT TCTGGAGAAT GCCTTTTGCA ACACTTTTCA GTAGCTGCCT GGAAACAACT       60

GCTTAGTCAT CGGTAGACAT TTAAAATATT CAAAATGTAT GGAGAATGGG GAATGGGGAA      120

TATCCTCATG ATGTTCCATG TGTACTTGGT GCAGGGCTTC AGGAGCGAAC ATGGACCAGT      180

GAAGCGATCA TCCCGGTCCA TGTTGGAACG ATCTGAACAA CAGATCCGAG CAGCTTCTAG      240

TTTGGAGGAG TTGCTGCAAA TCGCGCACTC TGAGGACTGG AAGCTGTGGC GATGCCGGTT      300

GAAGCTCAAA AGTCTTGCCA GTATGGACTC ACGCTCAGCA TCCCATCGCT CCACCAGATT      360

TGCGGCAACT TTCTATGACA CTGAAACACT AAAAGTTATA GATGAAGAAT GGCAGAGGAC      420

CCAATGCAGC CCTAGAGAGA CATGCGTAGA AGTCGCCAGT GAGCTGGGGA AGACAACCAA      480

CACATTCTTC AAGCCCCCCT GTGTAAATGT CTTCCGGTGT GGAGGCTGCT GCAACGAAGA      540

GGGTGTGATG TGTATGAACA CAAGCACCTC CTACATCTCC AAACAGCTCT TTGAGATATC      600

AGTGCCTCTG ACATCAGTGC CCGAGTTAGT GCCTGTTAAA ATTGCCAACC ATACGGGTTG      660

TAAGTGCTTG CCCACGGGCC CCGCCATCC TTACTCAATT ATCAGAAGAT CCATTCAGAC       720

CCCAGAAGAA GATGAATGTC CTCATTCCAA GAAACTCTGT CCTATTGACA TGCTGTGGGA      780

TAACACCAAA TGTAAATGTG TTTTGCAAGA CGAGACTCCA CTGCCTGGGA CAGAAGACCA      840

CTCTTACCTC AGGAACCCA CTCTCTGTGG ACCGCACATG ACGTTTGATG AAGATCGCTG       900

TGAGTGCGTC TGTAAAGCAC CATGTCCGGG AGATCTCATT CAGCACCCGG AAAACTGCAG      960

TTGCTTTGAG TGCAAAGAAA GTCTGGAGAG CTGCTGCCAA AAGCACAAGA TTTTTCACCC     1020
```

-continued

```
AGACACCTGC AGGTCAATGG TCTTTTCGCT TTCCCCTTAA CTTGGTTTAC TGATGACATT    1080

TAAAGGACAT ACTAATCTGA TCTGTTCAGG CTCTTTTCTC TCAGAGTCCA AGCAC         1135
```

(2) INFORMATION FOR SEQ ID NO:8:

(i) SEQUENCE CHARACTERISTICS:
        (A) LENGTH: 358 amino acids
        (B) TYPE: amino acid
        (C) STRANDEDNESS: single
        (D) TOPOLOGY: linear (ii) MOLECULE TYPE: protein (vi) ORIGINAL SOURCE:
        (F) TISSUE TYPE: Mouse Lung (xi) SEQUENCE DESCRIPTION: SEQ ID NO:8:

```
Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Asp Phe
            20                  25                  30

Ser Phe Glu Arg Ser Ser Arg Ser Met Leu Glu Arg Ser Glu Gln Gln
        35                  40                  45

Ile Arg Ala Ala Ser Ser Leu Glu Glu Leu Leu Gln Ile Ala His Ser
    50                  55                  60

Glu Asp Trp Lys Leu Trp Arg Cys Arg Leu Lys Leu Lys Ser Leu Ala
65                  70                  75                  80

Ser Met Asp Ser Arg Ser Ala Ser His Arg Ser Thr Arg Phe Ala Ala
                85                  90                  95

Thr Phe Tyr Asp Thr Glu Thr Leu Lys Val Ile Asp Glu Glu Trp Gln
            100                 105                 110

Arg Thr Gln Cys Ser Pro Arg Glu Thr Cys Val Glu Val Ala Ser Glu
        115                 120                 125

Leu Gly Lys Thr Thr Asn Thr Phe Phe Lys Pro Pro Cys Val Asn Val
    130                 135                 140

Phe Arg Cys Gly Gly Cys Cys Asn Glu Glu Gly Val Met Cys Met Asn
145                 150                 155                 160

Thr Ser Thr Ser Tyr Ile Ser Lys Gln Leu Phe Glu Ile Ser Val Pro
                165                 170                 175

Leu Thr Ser Val Pro Glu Leu Val Pro Val Lys Ile Ala Asn His Thr
            180                 185                 190

Gly Cys Lys Cys Leu Pro Thr Gly Pro Arg His Pro Tyr Ser Ile Ile
        195                 200                 205

Arg Arg Ser Ile Gln Thr Pro Glu Glu Asp Glu Cys Pro His Ser Lys
    210                 215                 220

Lys Leu Cys Pro Ile Asp Met Leu Trp Asp Asn Thr Lys Cys Lys Cys
225                 230                 235                 240

Val Leu Gln Asp Glu Thr Pro Leu Pro Gly Thr Glu Asp His Ser Tyr
                245                 250                 255

Leu Gln Glu Pro Thr Leu Cys Gly Pro His Met Thr Phe Asp Glu Asp
            260                 265                 270

Arg Cys Glu Cys Val Cys Lys Ala Pro Cys Pro Gly Asp Leu Ile Gln
        275                 280                 285

His Pro Glu Asn Cys Ser Cys Phe Glu Cys Lys Glu Ser Leu Glu Ser
    290                 295                 300

Cys Cys Gln Lys His Lys Ile Phe His Pro Asp Thr Cys Ser Cys Glu
305                 310                 315                 320
```

```
Asp Arg Cys Pro Phe His Thr Arg Thr Cys Ala Ser Arg Lys Pro Ala
                325                 330                 335

Cys Gly Lys His Trp Arg Phe Pro Lys Glu Thr Arg Ala Gln Gly Leu
            340                 345                 350

Tyr Ser Gln Glu Asn Pro
        355

(2) INFORMATION FOR SEQ ID NO:9:

(i) SEQUENCE CHARACTERISTICS:
        (A) LENGTH: 321 amino acids
        (B) TYPE: amino acid
        (C) STRANDEDNESS: single
        (D) TOPOLOGY: linear (ii) MOLECULE TYPE: protein (vi) ORIGINAL SOURCE:
        (F) TISSUE TYPE: Mouse Lung (xi) SEQUENCE DESCRIPTION: SEQ ID NO:9:

Met Tyr Gly Glu Trp Gly Met Gly Asn Ile Leu Met Met Phe His Val
1               5                   10                  15

Tyr Leu Val Gln Gly Phe Arg Ser Glu His Gly Pro Val Lys Arg Ser
            20                  25                  30

Ser Arg Ser Met Leu Glu Arg Ser Gln Gln Ile Arg Ala Ala Ser
        35                  40                  45

Ser Leu Glu Glu Leu Leu Gln Ile Ala His Ser Glu Asp Trp Lys Leu
    50                  55                  60

Trp Arg Cys Arg Leu Lys Leu Lys Ser Leu Ala Ser Met Asp Ser Arg
65                  70                  75                  80

Ser Ala Ser His Arg Ser Thr Arg Phe Ala Ala Thr Phe Tyr Asp Thr
                85                  90                  95

Glu Thr Leu Lys Val Ile Asp Glu Gly Trp Gln Arg Thr Gln Cys Ser
                100                 105                 110

Pro Arg Glu Thr Cys Val Glu Val Ala Ser Glu Leu Gly Lys Thr Thr
            115                 120                 125

Asn Thr Phe Phe Lys Pro Pro Cys Val Asn Val Phe Arg Cys Gly Gly
        130                 135                 140

Cys Cys Asn Glu Glu Gly Val Met Cys Met Asn Thr Ser Thr Ser Tyr
145                 150                 155                 160

Ile Ser Lys Gln Leu Phe Glu Ile Ser Val Pro Leu Thr Ser Val Pro
                165                 170                 175

Glu Leu Val Pro Val Lys Ile Ala Asn His Thr Gly Cys Lys Cys Leu
            180                 185                 190

Pro Thr Gly Pro Arg His Pro Tyr Ser Ile Ile Arg Arg Ser Ile Gln
        195                 200                 205

Thr Pro Glu Glu Asp Glu Cys Pro His Ser Lys Lys Leu Cys Pro Ile
    210                 215                 220

Asp Met Leu Trp Asp Asn Thr Lys Cys Lys Cys Val Leu Gln Asp Glu
225                 230                 235                 240

Thr Pro Leu Pro Gly Thr Glu Asp His Ser Tyr Leu Gln Glu Pro Thr
                245                 250                 255

Leu Cys Gly Pro His Met Thr Phe Asp Glu Asp Arg Cys Glu Cys Val
            260                 265                 270

Cys Lys Ala Pro Cys Pro Gly Asp Leu Ile Gln His Pro Glu Asn Cys
        275                 280                 285
```

```
Ser Cys Phe Glu Cys Lys Glu Ser Leu Glu Ser Cys Cys Gln Lys His
    290                 295                 300

Lys Ile Phe His Pro Asp Thr Cys Arg Ser Met Val Phe Ser Leu Ser
305                 310                 315                 320

Pro
```

(2) INFORMATION FOR SEQ ID NO:10:

(i) SEQUENCE CHARACTERISTICS:
        (A) LENGTH: 20 base pairs
        (B) TYPE: nuleic acid
        (C) STRANDEDNESS: single
        (D) TOPOLOGY: linear (ii) MOLECULE TYPE: oligonucleotide (vi) ORIGINAL SOURCE:
        (F) TISSUE TYPE:

(xi) SEQUENCE DESCRIPTION: SEQ ID NO:10:

GGGCTGCTTC TAGTTTGGAG      20

(2) INFORMATION FOR SEQ ID NO:11:

(i) SEQUENCE CHARACTERISTICS:
        (A) LENGTH: 20 base pairs
        (B) TYPE: nuleic acid
        (C) STRANDEDNESS: single
        (D) TOPOLOGY: linear (ii) MOLECULE TYPE: oligonucleotide (vi) ORIGINAL SOURCE:
        (F) TISSUE TYPE:

(xi) SEQUENCE DESCRIPTION: SEQ ID NO:11:

CACTCGCAAC GATCTTCGTC      20